US011627945B2

(12) United States Patent
Shidara

(10) Patent No.: US 11,627,945 B2
(45) Date of Patent: Apr. 18, 2023

(54) FAILURE PREDICTION SYSTEM OF ULTRASONIC ENDOSCOPE APPARATUS, FAILURE PREDICTION METHOD OF ULTRASONIC ENDOSCOPE APPARATUS, AND FAILURE PREDICTION PROGRAM OF ULTRASONIC ENDOSCOPE APPARATUS

(71) Applicant: FUJIFILM Corporation, Tokyo (JP)

(72) Inventor: Kenichi Shidara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 231 days.

(21) Appl. No.: 16/717,205

(22) Filed: Dec. 17, 2019

(65) Prior Publication Data
US 2020/0245979 A1 Aug. 6, 2020

(30) Foreign Application Priority Data

Jan. 31, 2019 (JP) .............................. JP2019-016088

(51) Int. Cl.
A61B 8/00 (2006.01)
A61B 8/12 (2006.01)
A61B 1/00 (2006.01)

(52) U.S. Cl.
CPC .................. *A61B 8/58* (2013.01); *A61B 8/12* (2013.01); *A61B 8/54* (2013.01); *A61B 1/00057* (2013.01); *A61B 2560/0276* (2013.01)

(58) Field of Classification Search
CPC .... A61B 8/58; A61B 8/12; A61B 8/54; A61B 1/00057; A61B 2560/0276; A61B 8/445; A61B 8/5207
See application file for complete search history.

(56) References Cited

U.S. PATENT DOCUMENTS 5,517,994 A * 5/1996 Burke .................. B06B 1/0622
600/437
2009/0299183 A1 12/2009 Kozai
(Continued)

FOREIGN PATENT DOCUMENTS

JP H06-269452 A 9/1994
JP H08-10257 A 1/1996
(Continued)

OTHER PUBLICATIONS

An Office Action; "Notice of Reasons for Refusal," mailed by the Japanese Patent Office dated Jan. 25, 2022, which corresponds to Japanese Patent Application No. 2019-016088 and is related to U.S. Appl. No. 16/717,205 with English language translation.
(Continued)

*Primary Examiner* — Christopher Koharski
*Assistant Examiner* — Taylor Deutsch
(74) *Attorney, Agent, or Firm* — Studebaker & Brackett PC

(57) ABSTRACT

Provided are a failure prediction system of an ultrasonic endoscope apparatus, a failure prediction method of the ultrasonic endoscope apparatus, and a non-transitory computer readable recording medium storing a failure prediction program of the ultrasonic endoscope apparatus capable of predicting a failure occurrence timing in the ultrasonic endoscope apparatus. A system controller includes an abnormality detection unit that acquires a reception signal of an ultrasonic vibrator of an ultrasonic endoscope and detects an abnormality of an ultrasonic endoscope apparatus including the ultrasonic endoscope, a storage control unit that stores information on the abnormality detected by the abnormality detection unit in association with time information, and a failure prediction unit that predicts a failure timing of the ultrasonic endoscope apparatus on the basis of the plurality (Continued)

of pieces of abnormality information stored by the storage control unit and time information corresponding the information.

18 Claims, 14 Drawing Sheets

(56) References Cited

U.S. PATENT DOCUMENTS

| | | | | |
|---|---|---|---|---|
| 2012/0271573 | A1* | 10/2012 | Markoff | G01R 31/66 |
| | | | | 702/59 |
| 2013/0194891 | A1* | 8/2013 | Kristoffersen | A61B 8/44 |
| | | | | 367/13 |
| 2017/0165837 | A1* | 6/2017 | Asano | B25J 9/1674 |
| 2018/0353061 | A1* | 12/2018 | Tanaka | A61B 1/00057 |

FOREIGN PATENT DOCUMENTS

| | | |
|---|---|---|
| JP | 2003-210458 A | 7/2003 |
| JP | 2009285175 A | 12/2009 |
| JP | 2013-154169 A | 8/2013 |

OTHER PUBLICATIONS

An Office Action; "Decision of Refusal," mailed by the Japanese Patent Office dated Jun. 21, 2022, which corresponds to Japanese Patent Application No. 2019-016088 and is related to U.S. Appl. No. 16/717,205 with English language translation.

* cited by examiner

FAILURE PREDICTION SYSTEM OF ULTRASONIC ENDOSCOPE APPARATUS, FAILURE PREDICTION METHOD OF ULTRASONIC ENDOSCOPE APPARATUS, AND FAILURE PREDICTION PROGRAM OF ULTRASONIC ENDOSCOPE APPARATUS

CROSS-REFERENCE TO RELATED APPLICATIONS

The present application claims priority under 35 U.S.C. § 119 to Japanese Patent Application No. 2019-016088, filed on Jan. 31, 2019. Each of the above application(s) is hereby expressly incorporated by reference, in its entirety, into the present application.

BACKGROUND OF THE INVENTION

1. Field of the Invention

The present invention relates to a failure prediction system of an ultrasonic endoscope apparatus, a failure prediction method of the ultrasonic endoscope apparatus, and a non-transitory computer readable recording medium storing a failure prediction program of the ultrasonic endoscope apparatus.

2. Description of the Related Art

An ultrasonic diagnosis apparatus that respectively drives a plurality of ultrasonic vibrators inside a subject (for example, a patient's body) and transmits and receives ultrasonic waves to acquire an ultrasound image inside the subject is already known (for example, see JP2009-285175A and JP1994-269452A (JP-H06-269452A)). JP2009-285175A and JP1994-269452A (JP-H06-269452A) disclose such an ultrasonic endoscope apparatus. The apparatus disclosed in JP2009-285175A and JP1994-269452A (JP-H06-269452A) performs abnormality detection such as disconnection on the basis of a reception signal of an ultrasonic vibrator in a case where ultrasonic waves are transmitted from the ultrasonic vibrator.

SUMMARY OF THE INVENTION

The ultrasonic endoscope apparatus includes an ultrasonic endoscope and a main body to which the ultrasonic endoscope is connected. Since the ultrasonic endoscope is expensive, it is desirable to be able to predict a failure timing before a serious failure occurs. Further, since the main body is also expensive and the main body is not easily replaceable, it is desirable to be able to predict a failure timing before a serious failure occurs, in the main body.

The abnormality detection method disclosed in JP2009-2851754 and JP1994-269452A (JP-H06-269452A) performs abnormality detection based on a reception signal measured at a specific timing. Accordingly, in a case where a serious failure occurs at the specific timing, the failure can be detected. However, in a state where such a failure does not occur, it is not possible to predict a failure occurrence timing in the future.

In consideration of the above-mentioned problems, an object of the invention is to provide a failure prediction system of an ultrasonic endoscope apparatus, a failure prediction method of the ultrasonic endoscope apparatus, and a non-transitory computer readable recording medium storing a failure prediction program of the ultrasonic endoscope apparatus capable of predicting a failure occurrence timing in the ultrasonic endoscope apparatus.

According to an aspect of the invention, there is provided a failure prediction system of an ultrasonic endoscope apparatus comprising: an abnormality detection unit that acquires a reception signal of an ultrasonic vibrator of an ultrasonic endoscope and detects an abnormality of the ultrasonic endoscope apparatus including the ultrasonic endoscope on the basis of the reception signal; a storage control unit that stores information on the abnormality detected by the abnormality detection unit in association with time information; and a failure prediction unit that predicts a failure timing of the ultrasonic endoscope apparatus on the basis of a plurality of pieces of the abnormality information stored by the storage control unit and the time information corresponding to the plurality of pieces of abnormality information.

According to another aspect of the invention, there is provided a failure prediction method of an ultrasonic endoscope apparatus, comprising: an abnormality detection step of acquiring a reception signal of an ultrasonic vibrator of an ultrasonic endoscope and detecting an abnormality of the ultrasonic endoscope apparatus including the ultrasonic endoscope on the basis of the reception signal; a storage control step of storing information on the abnormality detected in the abnormality detection step in association with time information; and a failure prediction step of predicting a failure timing of the ultrasonic endoscope apparatus on the basis of a plurality of pieces of the abnormality information stored in the storage control step and the time information corresponding to the plurality of pieces of abnormality information.

According to still another aspect of the invention, there is provided a non-transitory computer readable recording medium storing a failure prediction program of an ultrasonic endoscope apparatus, for causing a computer to execute: an abnormality detection step of acquiring a reception signal of an ultrasonic vibrator of an ultrasonic endoscope and detecting an abnormality of the ultrasonic endoscope apparatus including the ultrasonic endoscope on the basis of the reception signal; a storage control step of storing information on the abnormality detected in the abnormality detection step in association with time information; and a failure prediction step of predicting a failure timing of the ultrasonic endoscope apparatus on the basis of a plurality of pieces of the abnormality information stored in the storage control step and the time information corresponding to the plurality of pieces of abnormality information.

According to the invention, it is possible to provide a failure prediction system of an ultrasonic endoscope apparatus, a failure prediction method of the ultrasonic endoscope apparatus, and a non-transitory computer readable recording medium storing a failure prediction program of the ultrasonic endoscope apparatus capable of predicting a failure occurrence timing in the ultrasonic endoscope apparatus.

DESCRIPTION OF THE PREFERRED EMBODIMENTS

Overview of Ultrasonic Diagnosis Apparatus

Figure 1:
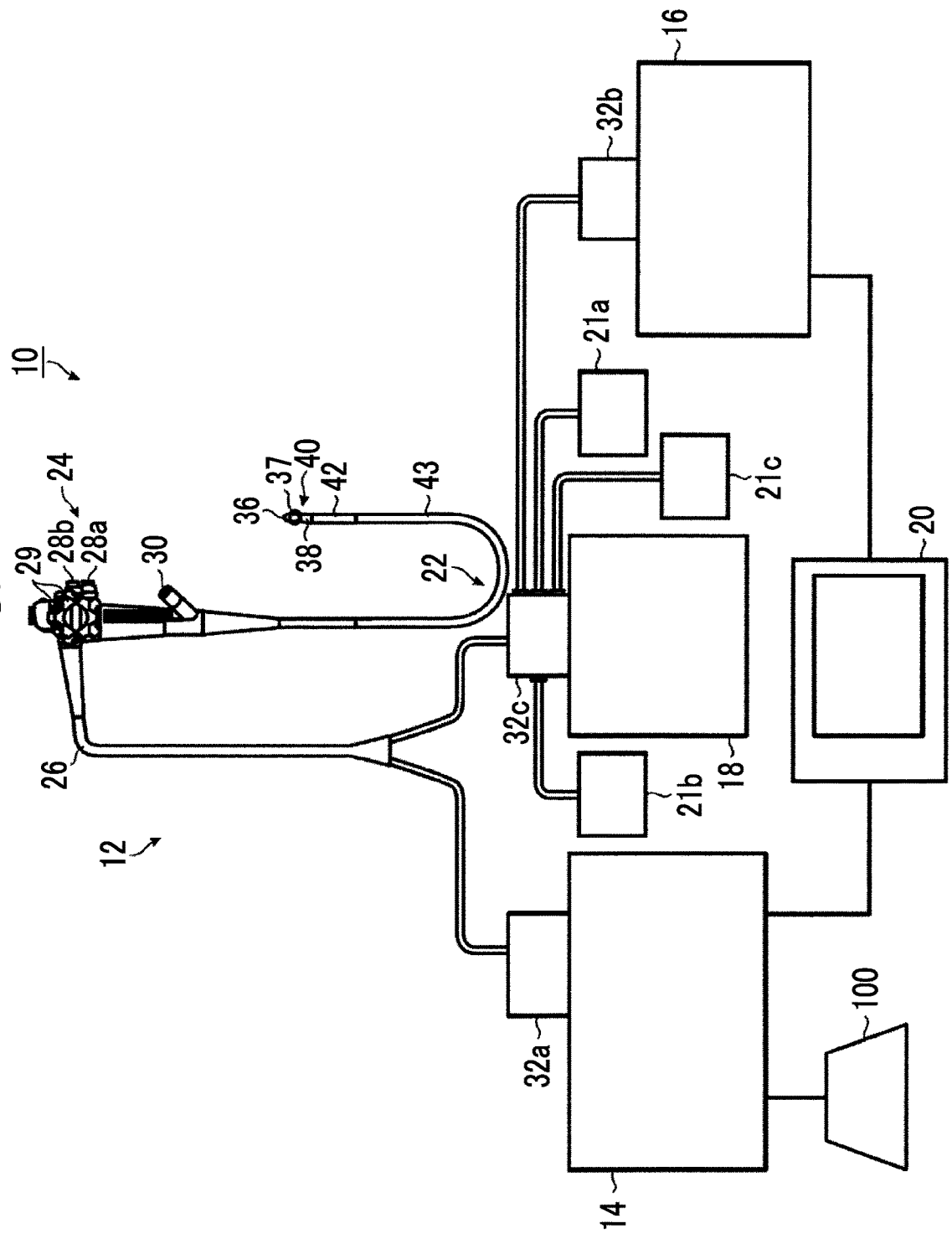
FIG. 1 is a diagram showing a schematic configuration of an ultrasonic endoscope apparatus 10.
Figure 2:
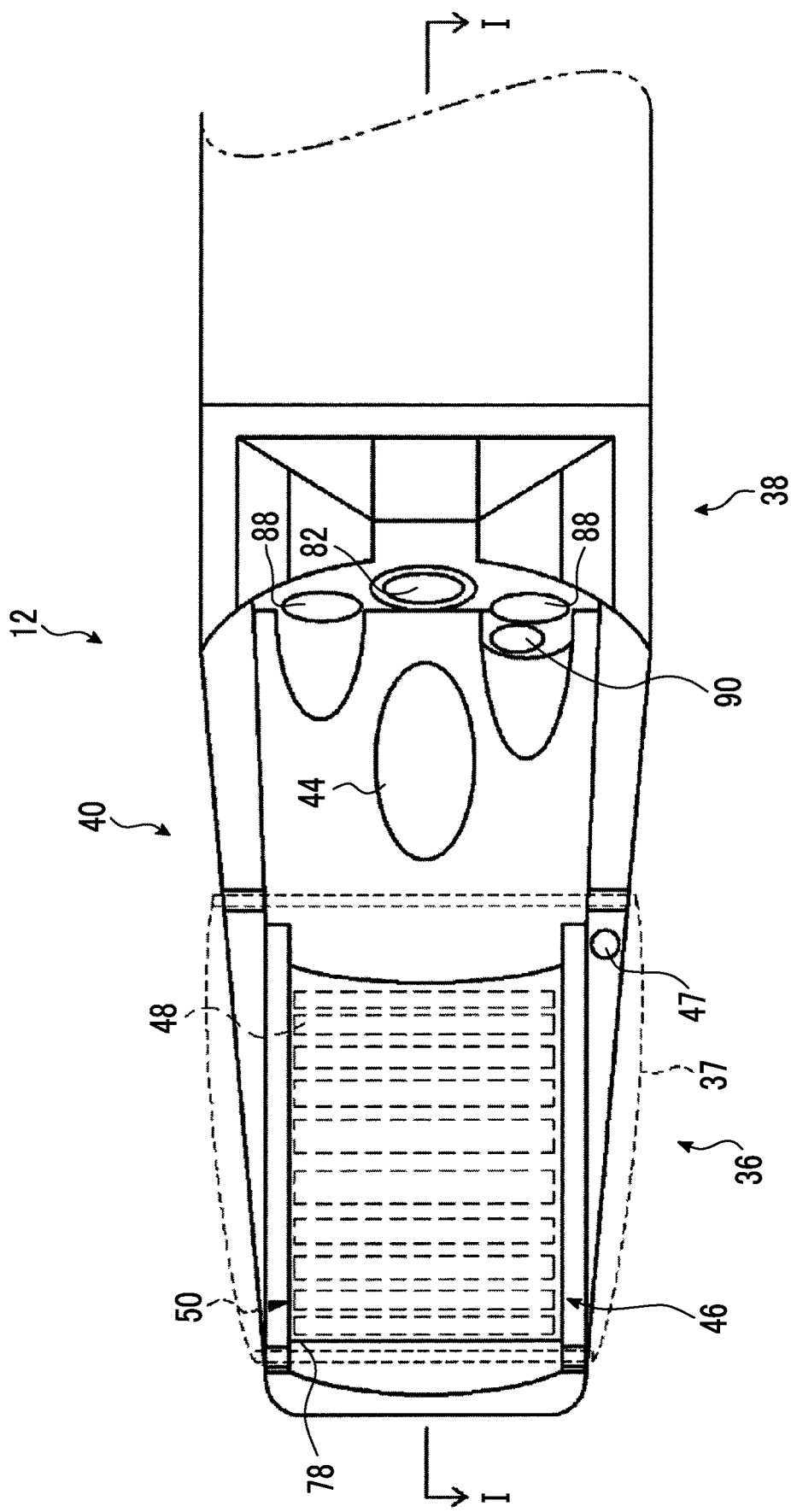
FIG. 2 is an enlarged plan view showing a distal end part of an insertion part 22 of an ultrasonic endoscope 12 and the vicinity thereof.
Figure 3:
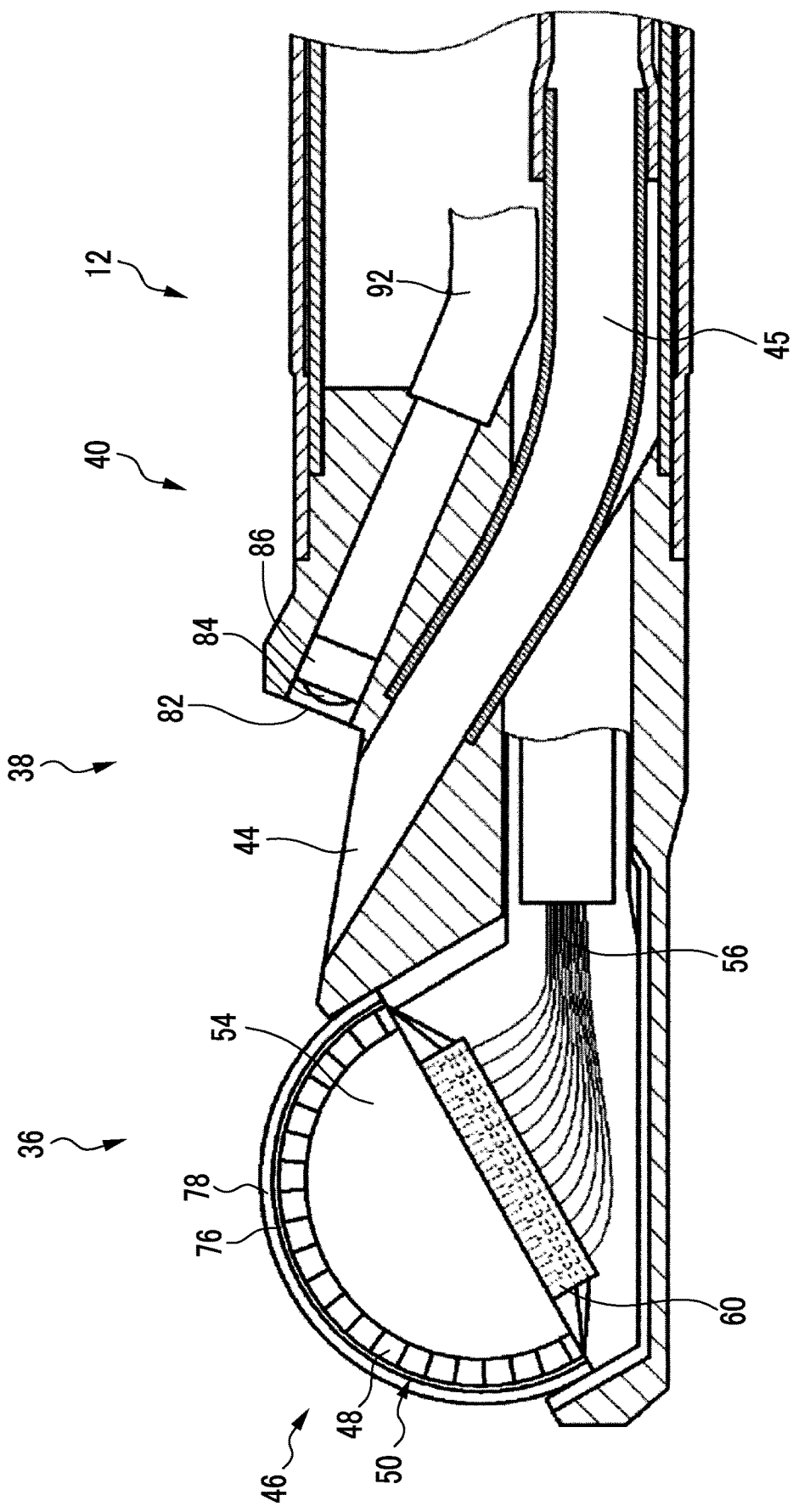
FIG. 3 is a diagram showing a cross section of a distal end part 40 of the insertion part 22 of the ultrasonic endoscope 12, taken along a section I-I shown in FIG. 2.
Figure 4:
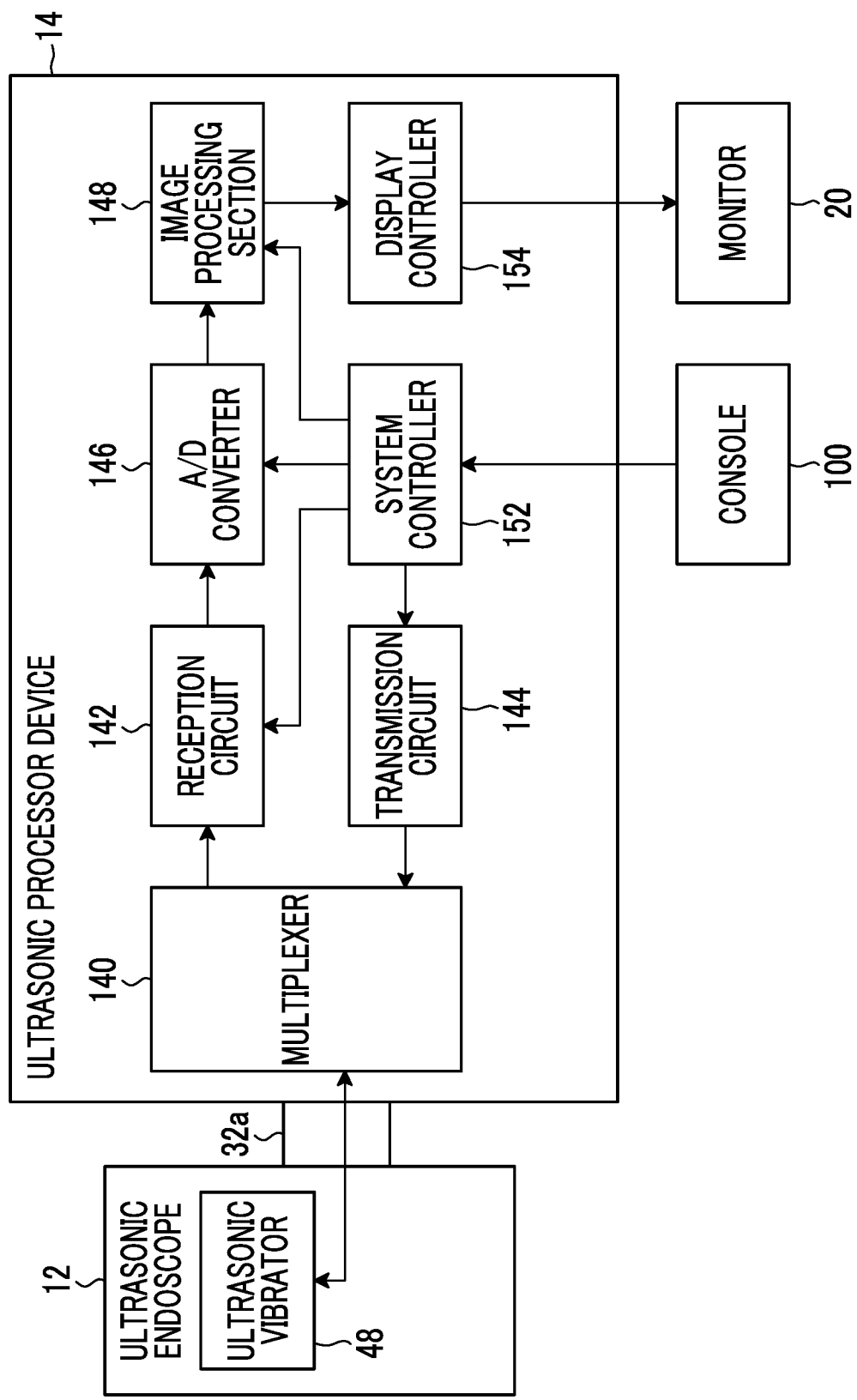
FIG. 4 is a block diagram showing a configuration of the ultrasonic endoscope 12 and an ultrasonic processor device 14.

An outline of an ultrasonic endoscope apparatus 10 including a failure prediction system according to an embodiment of the invention will be described with reference to FIGS. 1 to 4. FIG. 1 is a diagram showing a schematic configuration of the ultrasonic endoscope apparatus 10, FIG. 2 is an enlarged plan view of a distal end part of an insertion part 22 of an ultrasonic endoscope 12 and the vicinity thereof. In FIG. 2, for ease of illustration, a balloon 37 to be described later is shown by a broken line. FIG. 3 is a diagram showing a cross section of a distal end part 40 of the insertion part 22 of the ultrasonic endoscope 12, taken along a section I-I shown in FIG. 2. FIG. 4 is a block diagram showing a configuration of the ultrasonic endoscope 12 and the ultrasonic processor device 14.

The ultrasonic endoscope apparatus 10 is used for observing a state of an observation target portion in the body of a patient that is a subject using ultrasonic waves (hereinafter, referred to as ultrasonic diagnosis). Here, the observation target portion is a portion that is difficult to inspect from a body surface (outside) of the patient, which is the gallbladder or pancreas, for example. By using the ultrasonic endoscope apparatus 10, a state of the observation target portion and the presence or absence of an abnormality thereof may be ultrasonically diagnosed through the digestive tract such as the esophagus, stomach, duodenum, small intestine, and large intestine that are body cavities of the patient.

As shown in FIG. 1, the ultrasonic endoscope apparatus 10 includes the ultrasonic endoscope 12, an ultrasonic processor device 14, an endoscope processor device 16, a light source device 18, a monitor 20, and a console 100. Further, as shown in FIG. 1, a water supply tank 21a, a suction pump 21b, and an air supply pump 21c are provided as accessory devices of the ultrasonic endoscope apparatus 10. Further, a pipeline (not shown) that serves as a flow path for water and gas is formed in the ultrasonic endoscope 12. The ultrasonic processor device 14, the endoscope processor device 16, and the light source device 18 configure a main body of the ultrasonic endoscope apparatus 10.

As shown in FIG. 1, the ultrasonic endoscope 12 includes an insertion part 22 that is inserted into a body cavity of a patient, and an operation part 24 that is operated by an operator (user) such as a doctor or a technician. Further, as shown in FIGS. 2 and 3, an ultrasonic vibrator unit 46 including a plurality of ultrasonic vibrators 48 is attached to a distal end part 40 of the insertion part 22.

With the function of the ultrasonic endoscope 12, the operator may acquire an endoscope image of an inner wall of the body cavity of the patient and an ultrasound image of the observation target portion. The endoscope image is an image obtained by imaging the inner wall of the body cavity of the patient using an optical technique. The ultrasound image is an image obtained by receiving reflected waves (echoes) of ultrasonic waves transmitted from the body cavity of the patient toward the observation target portion and imaging a reception signal thereof.

The ultrasonic processor device 14 is connected to the ultrasonic endoscope 12 through a universal cord 26 and an ultrasound connector 32a provided at an end part thereof, as shown in FIG. 1. The ultrasonic processor device 14 controls the ultrasonic vibrator unit 46 of the ultrasonic endoscope 12 to transmit ultrasonic waves to the ultrasonic vibrator unit 46. Further, the ultrasonic processor device 14 images a reception signal in a case where the ultrasonic vibrator unit 46 receives reflected waves (echoes) of ultrasonic waves to generate an ultrasound image.

As shown in FIG. 1, the endoscope processor device 16 is connected to the ultrasonic endoscope 12 through the universal cord 26 and an endoscope connector 32b provided at an end part of the universal cord 26. The endoscope processor device 16 acquires image data of an observation target adjacent portion imaged by the ultrasonic endoscope 12 (specifically, an imaging element 86 to be described later), and performs predetermined image processing with respect to the acquired image data to generate an endoscope image. The observation target adjacent portion is a portion of the inner wall of the body cavity of the patient, which is adjacent to the observation target portion.

As shown in FIG. 1, the light source device 18 is connected to the ultrasonic endoscope 12 through the universal cord 26 and a light source connector 32c provided at the end part thereof. The light source device 18 emits white light, formed of three primary colors of red light, green light and blue light, or specific wavelength light in imaging the observation target adjacent portion using the ultrasonic endoscope 12. The light emitted from the light source device 18 propagates in the ultrasonic endoscope 12 through a light guide (not shown) included in the universal cord 26, and then, is emitted from the ultrasonic endoscope 12 (specifically, an illumination window 88 to be described later). Thus, the observation target adjacent portion is illuminated by the light from the light source device 18.

In this embodiment, the ultrasonic processor device 14 and the endoscope processor device 16 are configured by two devices (computers) that are separately provided. However, the invention is not limited to this configuration, and both the ultrasonic processor device 14 and the endoscope processor device 16 may be configured by a single device.

As shown in FIG. 1, the monitor 20 is connected to the ultrasonic processor device 14 and the endoscope processor device 16, and displays an ultrasound image generated by the ultrasonic processor device 14 and an endoscope image generated by the endoscope processor device 16. Regarding the display of the ultrasound image and the endoscope image, either one of the images may be switched and displayed on the monitor 20, or both the images may be simultaneously displayed. Further, a configuration in which the display methods are able to be discretionally selected or changed may be used.

In this embodiment, the ultrasound image and the endoscope image are displayed on one monitor 20, but an ultrasound image display monitor and an endoscope image display monitor may be separately provided. Further, a display form other than the monitor 20 may be used. For example, a form in which an ultrasound image and an endoscope image are displayed on a display of a personal terminal carried by an operator may be used.

The console 100 is an input device provided for an operator to input information necessary for ultrasonic diagnosis or for an operator to instruct the ultrasonic processor device 14 to start the ultrasonic diagnosis. The console 100 includes, for example, a keyboard, a mouse, a trackball, a touch pad, a touch panel, and the like, and is connected to a system controller 152 of the ultrasonic processor device 14 as shown in FIG. 4. In a case where the console 100 is operated, the system controller 152 of the ultrasonic processor device 14 controls each part of the device (for example, a reception circuit 142 and a transmission circuit 144 to be described later) according to the operation content.

The ultrasonic endoscope apparatus 10 configured as described above performs initialization for activation in a case where electric power is supplied. In a case where the ultrasonic endoscope 12 is connected to the main body at the same time as the electric power is supplied, the system controller 152 of the ultrasonic processor device 14 operates the ultrasonic endoscope 12 after the initialization to proceed to a live mode. The live mode is a mode for sequentially displaying (real-time display) ultrasound images (motion pictures) obtained at a predetermined frame rate. In a case where the ultrasonic endoscope 12 is not connected to the main body at a time point when the electric power is supplied, the system controller 152 of the ultrasonic processor device 14 operates the ultrasonic endoscope 12 at a time point when the ultrasonic endoscope 12 is connected thereto after the initialization to proceed to the live mode. In a state where the ultrasonic endoscope 12 is connected to the main body, it is possible to start the live mode at an unspecified timing (for example, a timing for starting inspection of a subject (a timing immediately before the ultrasonic endoscope 12 is inserted into the body cavity) by operating the console 100.

In the ultrasonic endoscope apparatus 10, at an unspecified timing in a period during which the ultrasonic endoscope 12 is not inserted into the body cavity in a state where the ultrasonic endoscope 12 is connected to the main body (in other words, in a period during which the ultrasonic endoscope 12 is not used), the ultrasonic processor device 14 performs a failure prediction process for predicting a failure of the ultrasonic endoscope apparatus 10. The failure prediction process will be described later.

The period during which the ultrasonic endoscope 12 is not used may be determined as follows, for example, 1) A period until an inspection starting instruction is performed by operating the console 100 after electric power is supplied is determined as the period during which the ultrasonic endoscope 12 is not used. 2) A period during Which a change in an endoscope image acquired from the ultrasonic endoscope 12 is small after electric power is supplied is determined as the period during which the ultrasonic endoscope 12 is not used. 3) A motion sensor such as an acceleration sensor is provided in the ultrasonic endoscope 12, and a period during which the amount of motion of the ultrasonic endoscope 12 is smaller than a predetermined value is determined as the period during which the ultrasonic endoscope 12 is not used. 4) A maintenance mode is provided in the ultrasonic endoscope apparatus 10, and a period during which the ultrasonic endoscope apparatus 10 is set to the maintenance mode is determined as the period during which the ultrasonic endoscope 12 is not used.

Configuration of Ultrasonic Endoscope

Next, a configuration of the ultrasonic endoscope 12 will be described with reference to FIGS. 1 to 4. The ultrasonic endoscope 12 includes the insertion part 22 and the operation part 24 as shown in FIG. 1. As shown in FIG. 1, the insertion part 22 includes the distal end part 40, a bending part 42, and a flexible part 43 in order from the distal end side (free end side). As shown in FIG. 2, the distal end part 40 is provided with an ultrasound observation part 36 and an endoscope observation part 38.

Further, as shown in FIGS. 2 and 3, the distal end part 40 is provided with a treatment instrument outlet 44. The treatment instrument outlet 44 serves as an outlet of a treatment instrument (not shown) such as a pair of forceps, a puncture needle, or a high-frequency knife, and also serves as a suction port for sucking a sucked substance such as blood and filth in the body.

Further, as shown in FIG. 2, a cleaning nozzle 90 formed to clean surfaces of an observation window 82 and an illumination window 88 is provided at the distal end part 40. Air or cleaning liquid is ejected from the cleaning nozzle 90 toward the observation window 82 and the illumination window 88.

Further, as shown in FIGS. 1 and 2, a balloon 37 that is able to be inflated and deflated is attached to the distal end part 40 at a position where the ultrasonic vibrator unit 46 is covered. The balloon 37 is disposed in the body cavity of the patient together with the ultrasonic vibrator unit 46. Then, water (specifically, de-aired water) as an ultrasonic transmission medium is injected into the balloon 37 from a water supply port 47 formed in the vicinity of the ultrasonic vibrator unit 46 at the distal end part 40, and thus, the balloon 37 is inflated. In a case where the inflated balloon 37 comes into contact with the inner wall of the body cavity (for example, around the observation target adjacent portion), air is excluded from between the ultrasonic vibrator unit 46 and the inner wall of the body cavity. Thus, it is possible to prevent attenuation of ultrasonic waves and their reflected waves (echoes) in the air.

As shown in FIG. 1, the bending part 42 is a part provided on a proximal end side (a side opposite to the side where the ultrasonic vibrator unit 46 is provided) with reference to the distal end part 40 in the insertion part 22, which is able to be freely bent. As shown in FIG. 1, the flexible part 43 is a part that connects the bending part 42 and the operation part 24, has flexibility, and is provided in an elongated state.

As shown in FIG. 1, the operation part 24 is provided with a pair of angle knobs 29 and a treatment instrument insertion port 30. In a case where each angle knob 29 is rotated, the bending part 42 is remotely operated to be bent and deformed. By this deformation operation, the distal end part 40 of the insertion part 22 provided with the ultrasound observation part 36 and the endoscope observation part 38 may be directed in a desired direction. The treatment instrument insertion port 30 is a hole formed for insertion of a treatment instrument such as a pair of forceps, and communicates with the treatment instrument outlet 44 through a treatment instrument channel 45 (see FIG. 3).

As shown in FIG. 1, the operation part 24 is provided with an air/water supply button 28a for opening or closing an air/water supply pipeline (not shown) that extends from a water supply tank 21a, and a suction button 28b for opening or closing a suction line (not shown) that extends from a suction pump 21b. A gas such as air sent from an air supply pump 21c and water in the water supply tank 21a flow through the air/water supply pipeline. In a case where the air/water supply button 28a is operated, a part to be opened of the air/water supply pipeline is switched, and gas and water ejecting outlets are also switched in a corresponding form between the cleaning nozzle 90 and the water supply port 47. That is, through the operation of the air/water supply button 28a, the cleaning of the endoscope observation part 38 and the inflation of the balloon 37 may be selectively performed.

The suction line is provided for sucking a sucked substance in the body cavity sucked from the cleaning nozzle 90 or for sucking the water in the balloon 37 through the water supply port 47. In a case where the suction button 28b is operated, a portion to be opened of the suction line is switched, and the suction port is also switched in a corresponding form between the cleaning nozzle 90 and the water supply port 47. That is, an object sucked by the suction pump 21b may be switched through the operation of the suction button 28b.

As shown in FIG. 1, at the other end of the universal cord 26, the ultrasound connector 32a connected to the ultrasonic processor device 14, the endoscope connector 32b connected to the endoscope processor device 16, and the light source connector 32c connected to the light source device 18 are provided. The ultrasonic endoscope 12 is detachably connected to the ultrasonic processor device 14, the endoscope processor device 16, and the light source device 18 through the connectors 32a, 32b, and 32c, respectively.

Next, among the components of the ultrasonic endoscope 12, the ultrasound observation part 36 and the endoscope observation part 38 will be described in detail.

Ultrasound Observation Part

The ultrasound observation part 36 is a part provided for acquiring an ultrasound image, and is disposed on the distal end side in the distal end part 40 of the insertion part 22 as shown in FIGS. 2 and 3. As shown in FIG. 3, the ultrasound observation part 36 includes the ultrasonic vibrator unit 46, a plurality of coaxial cables 56, and a flexible printed circuit (FPC) 60.

As shown in FIG. 3, the ultrasonic vibrator unit 46 is a convex probe in which a plurality of ultrasonic vibrators 48 are arranged in an arc shape, and transmits ultrasonic waves in a radial shape (arc shape). However, the type (model) of the ultrasonic vibrator unit 46 is not particularly limited, and may be any other type that can transmit and receive ultrasonic waves, for example, a sector type, a linear type, a radial type, and the like.

As shown in FIG. 3, the ultrasonic vibrator unit 46 is configured by laminating a backing material layer 54, an ultrasonic vibrator array 50, an acoustic matching layer 76, and an acoustic lens 78.

As shown in FIG. 3, the ultrasonic vibrator array 50 is configured of a plurality of ultrasonic vibrators 48 (ultrasonic transducers) that are arranged in a one-dimensional array shape. More specifically, the ultrasonic vibrator array 50 has a configuration in which N (for example, N=128) ultrasonic vibrators 48 are arranged in a convexly curved shape along an axial direction of the distal end part 40 (longitudinal axis direction of the insertion part at equal intervals. The ultrasonic vibrator array 50 may have a configuration in which the plurality of ultrasonic vibrators 48 are arranged in a two-dimensional array shape.

Each of the N ultrasonic vibrators 48 is configured by disposing electrodes on both surfaces of a single crystal vibrator that is a piezoelectric element.

As the single crystal vibrator, any one of quartz, lithium niobate, lead magnesium niobate (PMN), lead zinc niobate (PZN), lead indium niobate (PIN), lead titanate (PT), lithium tantalate, langasite, or zinc oxide may be used. The electrodes include individual electrodes (not shown) that are individually provided for each of the plurality of ultrasonic vibrators 48 and a ground electrode (not shown) common to the plurality of ultrasonic vibrators 48. Further, the electrodes are electrically connected to the ultrasonic processor device 14 through the coaxial cable 56 and the FPC 60.

Each ultrasonic vibrator 48 is supplied with a pulsed drive voltage as an input signal from the ultrasonic processor device 14 through the coaxial cable 56. In a case where the drive voltage is applied to the electrodes of the ultrasonic vibrator 48, the piezoelectric element expands and contracts, so that the ultrasonic vibrator 48 is driven (vibrated). As a result, pulsed ultrasonic waves are output from the ultrasonic vibrator 48.

Further, in a case where each ultrasonic vibrator 48 receives reflected waves of ultrasonic wave (echoes) or the like, the ultrasonic vibrator 48 vibrates (is driven) in accordance with the reflected waves, and the piezoelectric element of each ultrasonic vibrator 48 generates an electrical signal. The electric signal is output as a reception signal from each ultrasonic vibrator 48 toward the ultrasonic processor device 14.

As described above, the ultrasonic vibrator unit 46 of the present embodiment is a convex type. In other words, in this embodiment, the N ultrasonic vibrators 48 included in the ultrasonic vibrator unit 46 are sequentially driven by an electronic switch such as a multiplexer 140, so that the ultrasonic waves are scanned within a scanning range along a curved surface on which the ultrasonic vibrator array 50 is disposed, for example, a range of about several tens of millimeters from the center of curvature of the curved surface.

As shown in FIG. 3, the backing material layer 54 supports the ultrasonic vibrator array 50 from the back side (the side opposite to the acoustic matching layer 76). Further, the backing material layer 54 has a function of attenuating ultrasonic waves propagated toward the hack side of the ultrasonic vibrator array 50 among the ultrasonic waves emitted from the ultrasonic vibrator 48 or the ultrasonic waves (echoes) reflected from the observation target portion. A backing material is made of a material having rigidity such as hard rubber, in which an appropriate amount of an ultrasonic attenuating material (such as ferrite and ceramics) is added.

The acoustic matching layer 76 is provided to achieve acoustic impedance matching between the patient's body and a drive target vibrator. The acoustic matching layer 76 is disposed outside the ultrasonic vibrator array 50 (that is, the plurality of ultrasonic vibrators 48), and strictly speaking, is superimposed on the ultrasonic vibrator array 50 as shown in FIG. 3. By providing the acoustic matching layer 76, it is possible to increase transmittance of ultrasonic waves. As a material of the acoustic matching layer 76, various organic materials of which an acoustic impedance value is closer to that of the patient's body compared with the piezoelectric element of the ultrasonic vibrator 48 may be used. As the material of the acoustic matching layer 76, specifically, epoxy resin, silicone rubber, polyimide, polyethylene, and the like may be used.

The acoustic lens 78 is provided to converge ultrasonic waves emitted from the drive target vibrator toward the observation target portion, and is superimposed on the acoustic matching layer 76 as shown in FIG. 3. The acoustic lens 78 is made of, for example, a silicone resin (minable silicone rubber (HTV rubber), liquid silicone rubber (RTV rubber), or the like), a butadiene resin, a polyurethane resin, or the like, and powder of titanium oxide, alumina, silica, or the like may be mixed as necessary.

The FPC 60 is electrically connected to the electrodes provided in each ultrasonic vibrator 48. As shown in FIG. 3, each of the plurality of coaxial cables 56 is wired to the FPC 60 at one end thereof. In a case where the ultrasonic endoscope 12 is connected to the ultrasonic processor device 14 through the ultrasound connector 32a, each coaxial cable 56 is electrically connected to the ultrasonic processor device 14 at the other end thereof (on the side opposite to the FPC 60).

Endoscope Observation Part

The endoscope observation part 38 is a part provided for acquiring an endoscope image, and is disposed on a base end side with reference to the ultrasound observation part 36, in the distal end part 40 of the insertion part 22, as shown in FIGS. 2 and 3. As shown in FIGS. 2 and 3, the endoscope observation part 38 includes the observation window 82, an objective lens 84, the imaging element 86, the illumination window 88, the cleaning nozzle 90, a wiring cable 92, and the like.

As shown in FIG. 3, the observation window 82 is provided in a state of being inclined with respect to the axial direction (longitudinal axis direction of the insertion part 22), in the distal end part 40 of the insertion part 22. Light that is incident through the observation window 82 and is reflected by the observation target adjacent portion is imaged on an imaging surface of the imaging element 86 by the objective lens 84.

The imaging element 86 photoelectrically converts reflected light from the observation target adjacent portion that has passed through the observation window 82 and the objective lens 84 and is imaged on the imaging surface, and outputs an imaging signal. As the imaging element 86, a charge coupled device (CCD), a complementary metal oxide semiconductor (CMOS), or the like may be used. A captured image signal output by the imaging element 86 is transmitted to the endoscope processor device 16 by the universal cord 26 through the wiring cable 92 that elongates from the insertion part 22 to the operation part 24.

As shown in FIG. 2, the illumination window 88 is provided on both sides of the observation window 82. An emission end of a light guide (not shown) is connected to the illumination window 88. The light guide elongates from the insertion part 22 to the operation part 24, and an incident end thereof is connected to the light source device 18 connected through the universal cord 26. Illumination light emitted from the light source device 18 travels through the light guide, and is irradiated from the illumination window 88 toward the observation target adjacent portion.

Configuration of Ultrasonic Processor Device

As shown in FIG. 4, the ultrasonic processor device 14 includes the multiplexer 140, a reception circuit 142, a transmission circuit 144, an A/D converter 146, an image processing section 148, the system controller 152, and a display controller 154.

The reception circuit 142 and the transmission circuit 144 are electrically connected to the ultrasonic vibrator array 50 of the ultrasonic endoscope 12 through the multiplexer 140. The multiplexer 140 selects one or a plurality of ultrasonic vibrators 48 among N ultrasonic vibrators 48, and opens channels thereof.

The transmission circuit 144 is a circuit that supplies a drive voltage for ultrasonic transmission to the ultrasonic vibrator 48 selected by the multiplexer 140 in order to transmit ultrasonic waves from the ultrasonic vibrator unit 46. The drive voltage is a pulsed voltage signal, and is applied to the electrodes of the ultrasonic vibrator 48 to be driven through the universal cord 26 and the coaxial cable 56.

The reception circuit 142 is a circuit that receives an electrical signal output from the ultrasonic vibrator 48 that has received ultrasonic waves (echoes), that is, a reception signal. Further, the reception circuit 142 amplifies the reception signal received from the ultrasonic vibrator 48 in accordance with a control signal sent from the system controller 152, and delivers the amplified signal to the A/D converter 146. As shown in FIG. 4, the A/D converter 146 is connected to the reception circuit 142, converts a reception signal received from the reception circuit 142 from an analog signal to a digital signal, and outputs the converted digital signal to the image processing section 148.

The image processing section 148 is connected to the A/D converter 146 as shown in FIG. 4, and generates an ultrasound image based on a digital reception signal.

As shown in FIG. 4, the display controller 154 is connected to the image processing section 148, converts a signal of an ultrasound image generated by the image processing section 148 into an image signal based on a scan method of a normal television signal (raster conversion), performs a variety of necessary image processing such as gradation processing on the image signal, and outputs the image signal to the monitor 20.

The system controller 152 controls each section of the ultrasonic processor device 14, and is connected to the reception circuit 142, the transmission circuit 144, the A/D converter 146, and the image processing section 148 as shown in FIG. 4 to control these devices. As shown in FIG. 4, the system controller 152 is connected to the console 100, and controls each section of the ultrasonic processor device 14 in accordance with inspection information and control parameters input from the console 100 in inspecting a subject. Thus, an ultrasound image corresponding to an ultrasound image generation mode designated by the operator is acquired, and in particular, in the live mode, the ultrasound image is acquired at a constant frame rate as needed.

The system controller 152 includes various processors that execute processing by executing a program, a random access memory (RAM), and a read only memory (ROM).

The variety of processors in this specification may include a central processing unit (CPU) that is a general-purpose processor that executes a program to perform a variety of processing, a programmable logic device (PLD) that is a processor of which a circuit configuration is changeable after manufacturing, such as a field programmable gate array (FPGA), a dedicated electric circuit that is a processor having a circuit configuration that is dedicatedly designed for executing a specific process, such as an application specific integrated circuit (ASIC), or the like. More specifically, the structures of these various processors are electric circuits in which circuit elements such as semiconductor elements are combined.

The system controller 152 may be configured by one of various processors, or may be configured by a combination of two or more processors of the same type or different types (for example, a combination of a plurality of FPGAs or a combination of a CPU and an FPGA).

The system controller 152 performs the above-described failure prediction process at an unspecified timing in a period during which the ultrasonic endoscope 12 is not used in a state where the ultrasonic endoscope 12 is connected to the main body.

Figure 5:
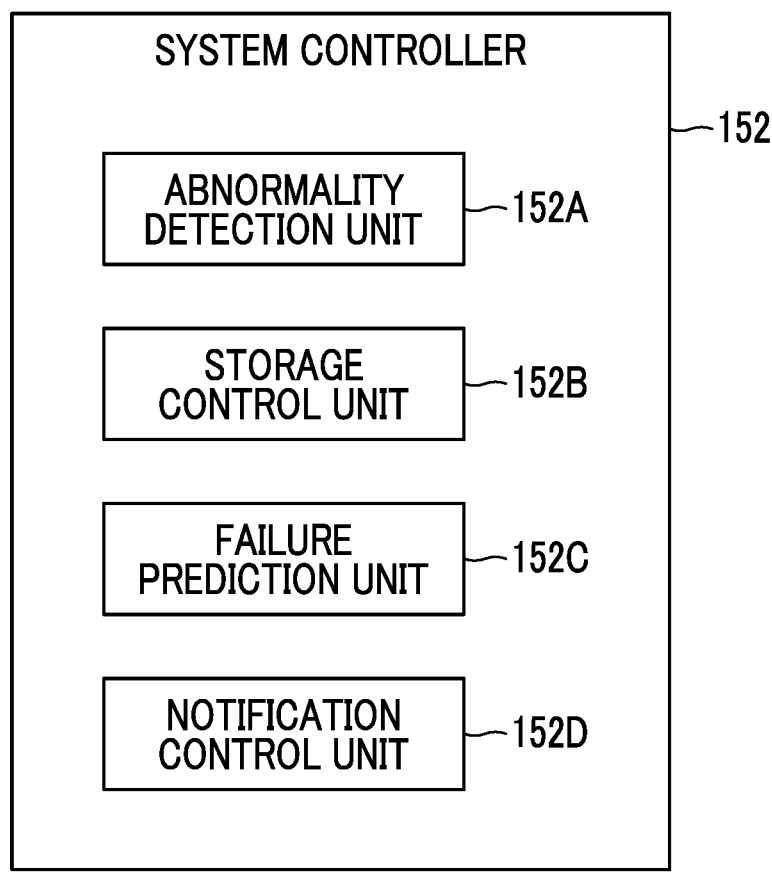
FIG. 5 is a diagram showing functional blocks of a system controller 152.

FIG. 5 is a diagram showing functional blocks of the system controller 152. A processor of the system controller 152 functions as an abnormality detection unit 152A, a storage control unit 152B, a failure prediction unit 152C, and a notification control unit 152D by executing a failure prediction program of the ultrasonic endoscope apparatus. A failure prediction process is executed by the functional blocks. In this embodiment, the system controller 152 configures a failure prediction system of the ultrasonic endoscope apparatus.

The abnormality detection unit 152A performs a process of selecting one from the N ultrasonic vibrators 48, transmitting ultrasonic waves from the selected ultrasonic vibrator 48, and acquiring a reception signal of the ultrasonic vibrator 48 that receives reflected waves of the ultrasonic waves, with respect to all the ultrasonic vibrators 48 while sequentially switching the selected ultrasonic vibrator 48. With this process, a reception signal is acquired from each of the N ultrasonic vibrators 48. The abnormality detection unit 152A detects an abnormality of the ultrasonic endoscope apparatus 10 on the basis of N reception signals acquired in this way.

In this embodiment, the abnormality of the ultrasonic endoscope apparatus 10 refers to a state where the ultrasonic vibrator 48 is deteriorated, a state where a wire that connects the ultrasonic vibrator 48 and the ultrasonic processor device 14 is damaged, or the like.

For example, in a case where disconnection occurs in the coaxial cable 56, a reception signal of the ultrasonic vibrator 48 connected to the coaxial cable 56 with the disconnection changes compared with a reception signal of the ultrasonic vibrator 48 connected to the coaxial cable 56 without disconnection. Specifically, a period of time taken from the time when the level of a reception signal reaches a peak to the time when the level becomes equal to or smaller than a predetermined value is shorter in the coaxial cable 56 with the disconnection compared with in the coaxial cable 56 without the disconnection. Accordingly, it is possible to determine the presence or absence of disconnection by viewing the period of time. The abnormality detection method by the abnormality detection unit 152A is not limited to the above-described example, and may employ any different method.

The abnormality detection unit 152A determines the presence or absence of an abnormality for each of the N reception signals, and outputs the number of times of the abnormality determination (hereinafter, referred to as an abnormality occurrence number) as detected abnormality information. In the ultrasonic endoscope apparatus 10, it is possible to use not only one ultrasonic endoscope 12, but also, to use a plurality of ultrasonic endoscopes 12 in a switchable manner. Although the plurality of ultrasonic endoscopes 12 are the same model, there are individual differences. Further, there is a difference in characteristics such as reception sensitivity of the ultrasonic endoscope 12 even in the same model. Accordingly, it is preferable that a determination criterion for determining that the abnormality detection unit 152A is abnormal is not common to all the ultrasonic endoscopes 12 capable of being connected to the main body, and is individually determined for each ultrasonic endoscope 12.

The storage control unit 152B stores abnormality information output from the abnormality detection unit 152A in a ROM inside the system controller 152 in association with time information and identification information of the ultrasonic endoscope 12 connected to the main body. The time information is information indicating a point in time when an abnormality is detected, which is the date and time when the abnormality information is output from the abnormality detection unit 152A, for example. Hereinafter, the abnormality information stored in the ROM and corresponding time information are collectively referred to as abnormality log information.

In a case where the ultrasonic endoscope 12 is connected to the main body, the storage control unit 152B may acquire identification information from the ultrasonic endoscope 12, and may recognize the identification information of the ultrasonic endoscope 12. In this way, in a case where a plurality of ultrasonic endoscopes 12 are used, abnormality log information of each different ultrasonic endoscope 12 is stored in the ROM.

The failure prediction unit 152C predicts a failure timing of the ultrasonic endoscope apparatus 10 on the basis of a plurality of pieces of abnormality log information corresponding to each identification information stored in the ROM by the storage control unit 152B.

Figure 6:
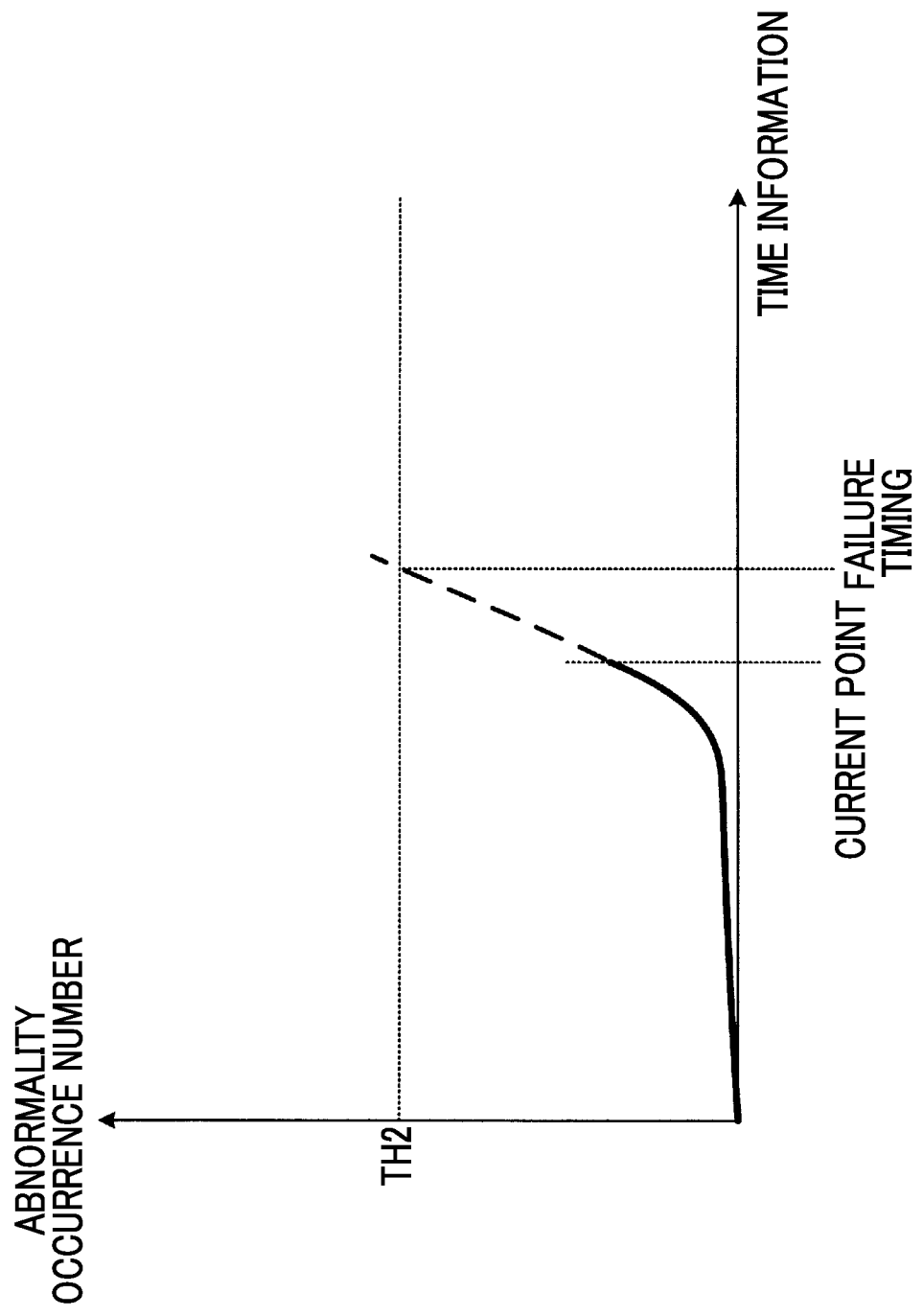
FIG. 6 is a graph showing an example of abnormality log information corresponding to unspecified identification information.

FIG. 6 is a graph showing an example of abnormality log information corresponding to unspecified identification information. In FIG. 6, a lateral axis represents time information included in abnormality log information and a longitudinal axis represents abnormality information (abnormality occurrence number) included in the abnormality log information. A threshold value TH2 shown in FIG. 6 is a lower limit value of the abnormality occurrence number capable of determining that the ultrasonic endoscope 12 is in failure.

In the ultrasonic endoscope apparatus 10, even in a case where an abnormality occurs in a reception signal of the ultrasonic vibrator 48, in generating an ultrasound image, the reception signal may be interpolated by a reception signal of the ultrasonic vibrator 48 around the ultrasonic vibrator 48 to thus be corrected. For example, an abnormality occurrence number in a case where the quality of the ultrasound image cannot be ensured by such correction may be set as the threshold value TH2.

For example, in a case where there is almost no change in an abnormality occurrence number based on the abnormality log information (for example, in a case where the size of an inclination of an approximate straight line obtained from the abnormality log information by the least squares method is equal to or smaller than a predetermined value), the failure prediction unit 152C determines that a date obtained by adding a service life in normal use set in the ultrasonic endoscope 12 to a date based on the oldest time information included in the abnormality log information as a failure timing at which failure of the ultrasonic endoscope 12 occurs.

For example, in a case where a large increase tendency is observed in the abnormality occurrence number based on the abnormality log information (for example, in a case where the inclination of the approximate straight line exceeds the predetermined value), on the basis of the increase tendency, the failure prediction unit 152C determines a timing (failure timing in FIG. 6) at which the abnormality occurrence number will reach the threshold value TH2 in the future (at which the ultrasonic endoscope 12 will fail) in a case where a usage frequency and a usage way until a current time point are continued.

The failure prediction unit 152C outputs the failure timing of the ultrasonic endoscope 12 determined as described above as a prediction result.

The notification control unit 152D shown in FIG. 5 performs a notification process based on the prediction result of the failure prediction unit 152C. For example, the notification control unit 152D sets a timing before a predetermined period of the failure timing indicated by the prediction result as a recommended maintenance timing, and displays a message indicating the recommended maintenance timing on the monitor 20 to notify a user of the recommended maintenance timing. Content of the message may be the failure timing itself, or may indicate a remaining period until failure.

The notification control unit 152D may output the message through a speaker (not shown) provided in the ultrasonic endoscope apparatus 10, instead of displaying the message on the monitor 20, Alternatively, the notification control unit 152D transmits the message to an external electronic device connected to the ultrasonic endoscope apparatus 10 to notify an administrator or the user of the ultrasonic endoscope apparatus 10 of the recommended maintenance timing.

Figure 7:
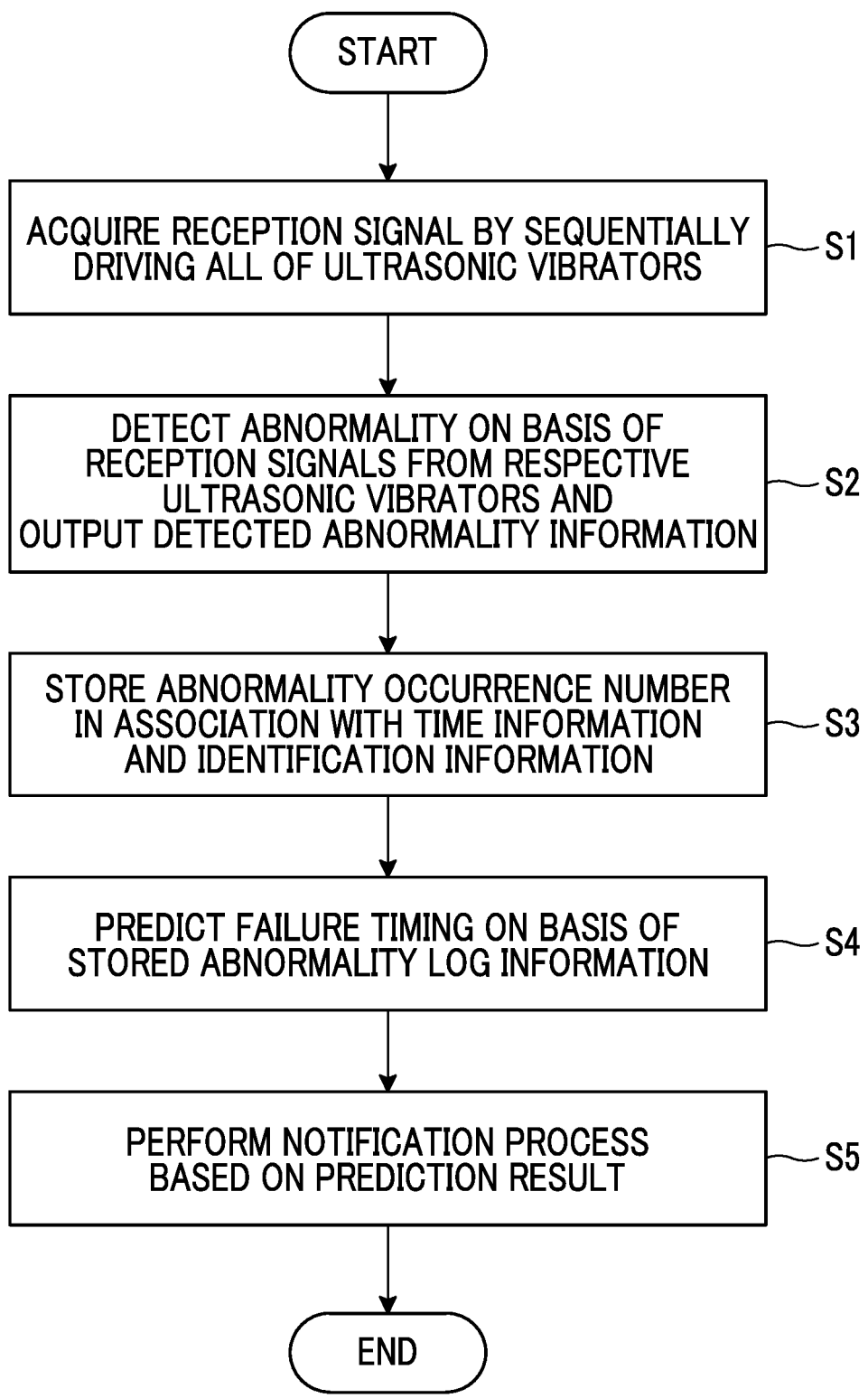
FIG. 7 is a flowchart for illustrating an operation of a failure prediction process of the system controller 152.

FIG. 7 is a flowchart for illustrating an operation of the failure prediction process of the system controller 152. First, the abnormality detection unit 152A sequentially drives the N ultrasonic vibrators 48, sequentially transmits ultrasonic waves from the respective N ultrasonic vibrators 48, and acquires a reception signal of reflected waves of the ultrasonic waves from each ultrasonic vibrator 48 (step S1).

Then, the abnormality detection unit 152A detects an abnormality that occurs in the ultrasonic endoscope 12 on the basis of each of the N reception signals acquired in step S1, and outputs the abnormality occurrence number as abnormality information (step S2).

Then, the storage control unit 152B stores the abnormality information output from the abnormality detection unit 152A in the ROM in association with time information at a current point in time and identification information (hereinafter, referred to as identification information ID1) of the ultrasonic endoscope 12 connected to the main body (step S3).

Then, the failure prediction unit 1520 predicts a failure timing of the ultrasonic endoscope 12 having identification information ID1 connected to the main body, on the basis of the entire abnormality log information (abnormality information and time information) corresponding to the identification information ID1 stored in the ROM (step S4).

In a case where the failure timing is predicted in step S4, the notification control unit 152D performs the notification process based on the prediction result (step S5). The above-described series of processes are performed whenever the ultrasonic endoscope 12 is connected to the main body, for example. Further, as the abnormality log information stored in the ROM increases, the prediction accuracy of the failure timing is also improved.

As described above, according to the ultrasonic endoscope apparatus 10, it is possible to predict the failure timing of the ultrasonic endoscope 12 on the basis of a history of the abnormality occurrence number detected on the basis of the reception signals of the ultrasonic vibrators 48 of the ultrasonic endoscope 12. Thus, it is possible to predict the failure timing, to thereby propose an appropriate maintenance timing to the user. As a result, for example, it is possible to expect execution of maintenance before failure occurs, and to lengthen the life of the ultrasonic endoscope 12. Further, in a case where the abnormality occurrence number does not increase, it is possible to postpone the maintenance timing, and to reduce the number of maintenances to reduce a period of time during which the ultrasonic endoscope 12 cannot be used.

In this embodiment, a configuration in which the abnormality detection unit 152A outputs an abnormality occurrence number as abnormality information has been described. As a modification thereof, the abnormality detection unit 152A calculates an abnormality occurrence rate that is a ratio of the abnormality occurrence number to N or an abnormality non-occurrence rate that is a ratio of (N−abnormality occurrence number) to N, and may output the result as abnormality information. In this case, the failure prediction unit 152C may predict, in a case where the abnormality occurrence rate tends to increase, a failure timing based on the increase tendency. Further, in a case where the failure non-occurrence rate tends to decrease, the failure prediction unit 152C may predict the failure timing based on the decrease tendency.

The abnormality detection unit 152A, the storage control unit 152B, the failure prediction unit 152C, and the notification control unit 152D of the system controller 152 may be configured to be provided in a processor included in the endoscope processor device 16. In this configuration, the failure prediction system of the ultrasonic endoscope apparatus is configured by the processor included in the endoscope processor device 16.

Alternatively, among the functional blocks of the system controller 152, the failure prediction unit 152C and the notification control unit 152D may be provided in a processor included in an external device such as an external server connectable to the ultrasonic endoscope apparatus 10. In this configuration, the storage control unit 152B of the system controller 152 may transmit abnormality log information and identification information to the external device, so that the abnormality log information and the identification information may be stored in a database in the external device.

Thus, the processor of the external device can predict the failure tuning for each ultrasonic endoscope 12 specified by the identification information on the basis of the abnormality log information stored in the database. Further, according to this configuration, it is possible to cope with a case where one ultrasonic endoscope 12 is used by a plurality of ultrasonic endoscope apparatuses 10 as in a large hospital or the like. In this configuration, the system controller 152 of the ultrasonic processor device 14 and the processor of the external device configure the failure prediction system of the ultrasonic endoscope apparatus.

Hereinafter, modification examples of the ultrasonic endoscope apparatus 10 will be described.

First Modification Example

Figure 8:
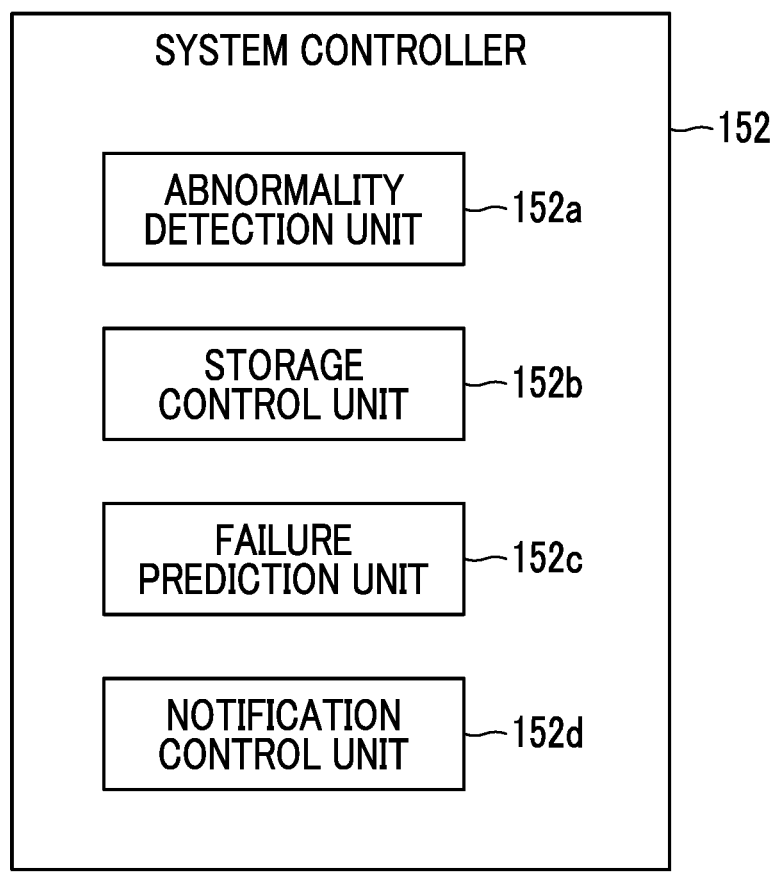
FIG. 8 is a diagram showing functional blocks of the system controller 152 in the ultrasonic endoscope apparatus 10 according to a first modification example.

FIG. 8 is a diagram showing functional blocks of the system controller 152 in the ultrasonic endoscope apparatus 10 according to a first modification example. A processor of the system controller 152 shown in FIG. 8 executes the failure prediction program for the ultrasonic endoscope apparatus to function as an abnormality detection unit 152a, a storage control unit 152b, a failure prediction unit 152c, and a notification control unit 152d. The failure prediction process is executed by the functional blocks. In the first modification example, the system controller 152 forms the failure prediction system of the ultrasonic endoscope apparatus.

The abnormality detection unit 152a performs a process of controlling each of the N ultrasonic vibrators 48 so as not to transmit ultrasonic waves, selecting the N ultrasonic vibrators 48 one by one, and acquiring a reception signal of the selected ultrasonic vibrator 48. In this process, among a period during which each ultrasonic vibrator 48 is driven in a control sequence of the ultrasonic vibrator unit 46 in a case where an ultrasound image corresponding to one frame is acquired in a live mode or the like, and a period during which a reception signal thereafter is output, the former period is replaced with a period during which each ultrasonic vibrator 48 is not driven. Further, in this process, in a period during obtained by combining the period during which the ultrasonic vibrator 48 is not driven and a subsequent output period, a reception signal output from the ultrasonic vibrator 48 is acquired. The abnormality detection unit 152a detects an abnormality of the ultrasonic endoscope apparatus 10 on the basis of the N reception signals acquired from the respective ultrasonic vibrators 48 in this way.

Figure 9:
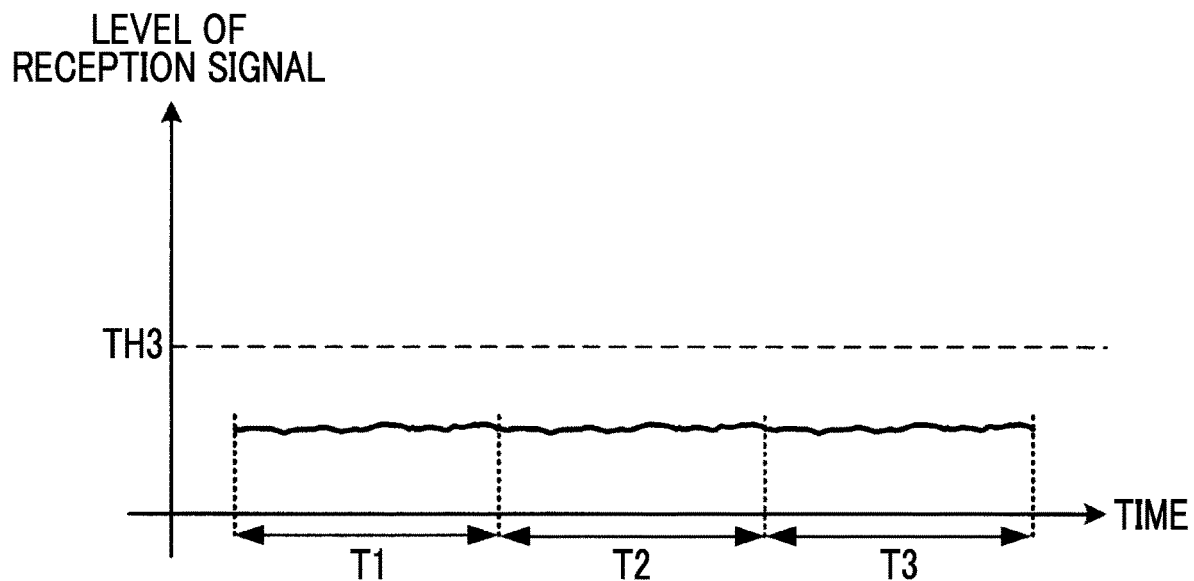
FIG. 9 is a diagram showing an example of a reception signal acquired in a case where ultrasonic waves are not transmitted.

The abnormality of the ultrasonic endoscope apparatus 10 of the first modification example refers to noise mixture in a reception signal caused by various factors such as an abnormality of a device included in the ultrasonic endoscope 12 or an abnormality of a device of a power source or the like in the main body of the ultrasonic endoscope apparatus 10, FIG. 9 is a diagram showing an example of a reception signal acquired in a case where ultrasonic waves are not transmitted. As shown in FIG. 9, the abnormality detection unit 152a performs the above-described process, so that reception signals are acquired in the order of a period T1, a period T2, a period T3, and so on. The length of a period during which each reception signal is output is the same as a length obtained by combining the period during which each ultrasonic vibrator 48 is driven in the control sequence for generating an ultrasound image and the period during which the reception signal thereafter is output. In a case where no abnormality occurs in the ultrasonic endoscope apparatus 10, as shown in FIG. 9, each of the N reception signals is in a stable state at a low level.

Figure 10:
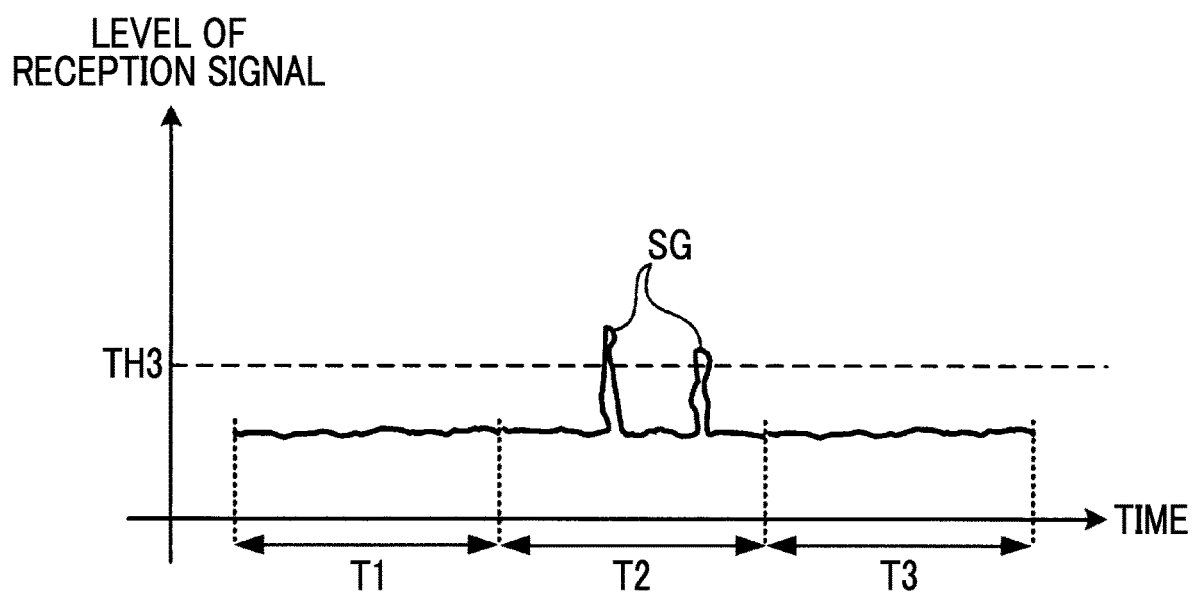
FIG. 10 is a diagram showing an example of a case where noise is superimposed in a reception signal acquired in a case where ultrasonic waves are not transmitted.

However, in a case where an abnormality occurs in the ultrasonic endoscope apparatus 10, as shown in FIG. 10, a state where a noise signal SG of a level that exceeds a predetermined threshold value TH3 is included in a reception signal occurs.

The abnormality detection unit 152a determines whether or not each of the N reception signals acquired in a state where ultrasonic waves are not transmitted includes the noise signal SG that exceeds the threshold value TH3, sets the number of reception signals for which it is determined that the noise signal SG is included as an abnormality occurrence number, and outputs information on the abnormality occurrence number as information on the detected abnormality. The threshold value TH3 forms a first threshold value.

It is preferable that the threshold value TH3 is not common to all the ultrasonic endoscopes 12 connectable to the main body and is individually determined for each ultrasonic endoscope 12.

The storage control unit 152b shown in FIG. 8 stores abnormality information output from the abnormality detection unit 152a in a ROM inside the system controller 152 in association with time information and identification information of the ultrasonic endoscope 12 connected to the main body. The time information is information indicating a time point when an abnormality is detected by the abnormality detection unit 152a, for example, which is the date and time when the abnormality information is output from the abnormality detection unit 152a. In this modification example, similarly, abnormality information stored in the ROM and corresponding time information are collectively referred to as abnormality log information.

In a case where the ultrasonic endoscope 12 is connected to the main body, the storage control unit 152b shown in FIG. 8 may acquire identification information from the ultrasonic endoscope 12, and may recognize the identification information of the ultrasonic endoscope 12. In this way, in a case where a plurality of ultrasonic endoscopes 12 are used, abnormality log information of each different ultrasonic endoscope 12 is stored in the ROM.

The failure prediction unit 152c shown in FIG. 8 predicts a failure timing of the ultrasonic endoscope apparatus 10 on the basis of a plurality of pieces of abnormality log information corresponding to each piece of identification information stored in the ROM by the storage control unit 152b.

Figure 11:
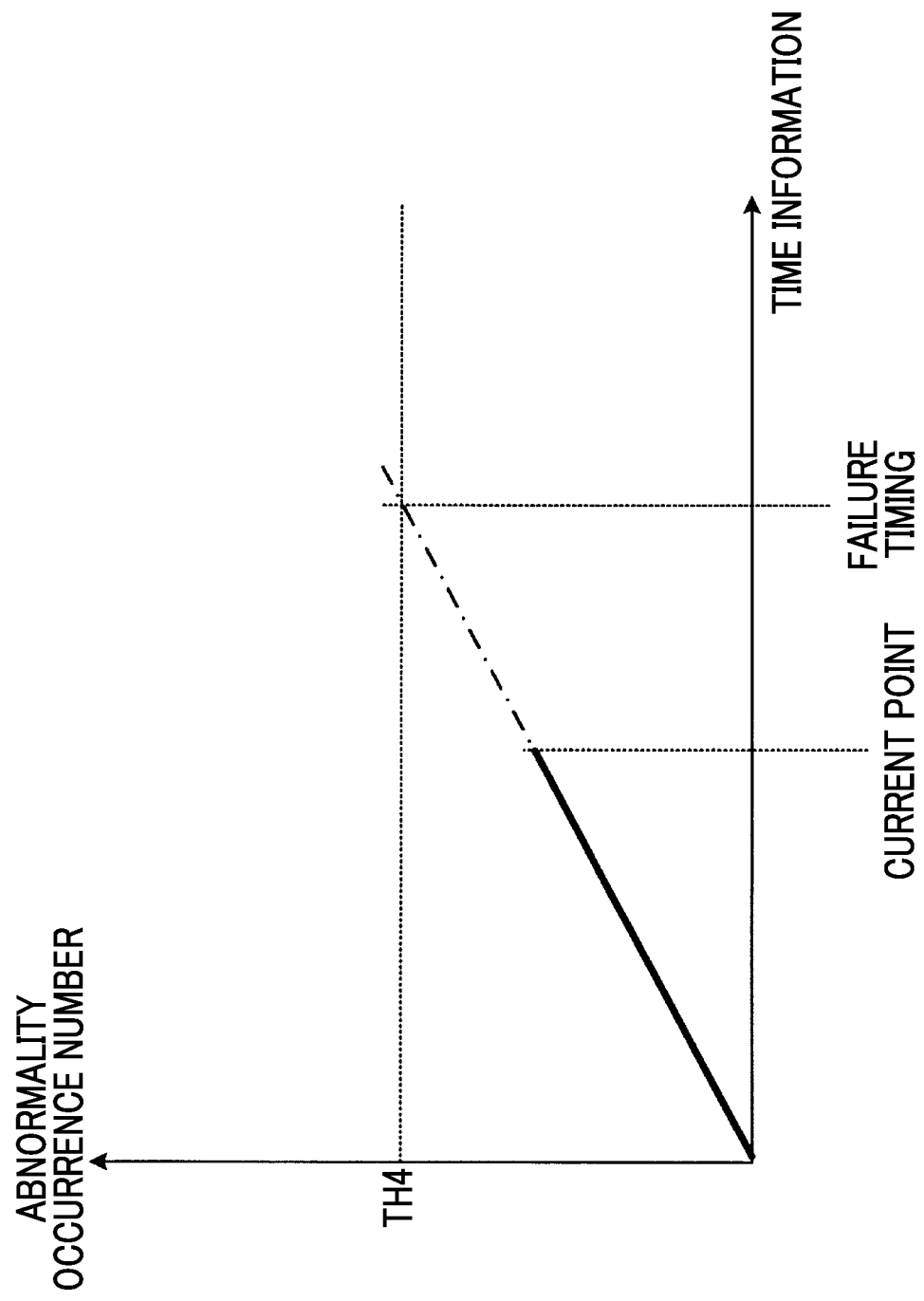
FIG. 11 is a graph showing an example of abnormality log information corresponding to unspecified identification information.

FIG. 11 is a graph showing an example of abnormality log information corresponding to unspecified identification information. In FIG. 11, a lateral axis represents time information included in abnormality log information and a longitudinal axis represents abnormality information (abnormality occurrence number) included in the abnormality log information. A threshold value TH4 shown in FIG. 11 is a lower limit value of the abnormality occurrence number capable of determining that the ultrasonic endoscope apparatus 10 is in failure.

In the ultrasonic endoscope apparatus 10, even in a case where noise is mixed in a reception signal of the ultrasonic vibrator 48, it is possible to perform noise elimination for eliminating the noise in generating an ultrasound image. For example, an abnormality occurrence number in a case where the quality of an ultrasound image cannot be ensured by the above-described noise elimination is set as a threshold value TH4.

For example, in a case where there is almost no change in an abnormality occurrence number based on the abnormality log information (for example, in a case where an inclination of an approximate straight line of the abnormality occurrence number obtained from the abnormality log information by the least squares method is equal to or smaller than a predetermined value), the failure prediction unit 152c determines that a date obtained by adding a service life in normal use set in the ultrasonic endoscope 12 to a date based on the oldest time information included in the abnormality log information as a failure timing at which failure of the ultrasonic endoscope 12 occurs. Further, the failure prediction unit 152c determines a timing obtained by adding a time obtained by subtracting an accumulated usage time at a current time point of the ultrasonic endoscope apparatus 10 from an accumulated usable time in normal use that is determined in advance with respect to the ultrasonic endoscope apparatus 10 (a usable time until maintenance is necessary) to the current time point, as a failure timing at which failure of the main body of the ultrasonic endoscope apparatus 10 occurs.

For example, in a case where there is a large increase tendency in the abnormality occurrence number based on the abnormality log information (for example, in a case where the inclination of the approximate straight line exceeds the predetermined value), on the basis of the increase tendency, the failure prediction unit 152c determines a timing (failure timing in FIG. 11) at which the abnormality occurrence number will reach the threshold value TH4 in the future (at which the ultrasonic endoscope apparatus 10 will fail) in a case where a usage frequency and a usage way up to a current time point are continued.

The failure prediction unit 152c outputs the failure timing of the ultrasonic endoscope apparatus 10 determined as described above as a prediction result.

The notification control unit 152d shown in FIG. 8 performs a notification process based on the prediction result of the failure prediction unit 152c. For example, the notification control unit 152d sets a timing before a predetermined period of the failure timing indicated by the prediction result as a recommended maintenance timing, and displays a message indicating the recommended maintenance timing on the monitor 20 to notify the user of the recommended maintenance timing of the ultrasonic endoscope apparatus 10. Content of the message may be the failure timing itself, or may indicate a remaining period until failure. The notification control unit 152d may output the message through a speaker shown) provided in the ultrasonic endoscope apparatus 10, instead of displaying the message on the monitor 20. Alternatively, the notification control unit 152d transmits the message to an external electronic device connected to the ultrasonic endoscope apparatus 10 to notify an administrator or the user of the ultrasonic endoscope apparatus 10 of the recommended maintenance timing.

Figure 12:
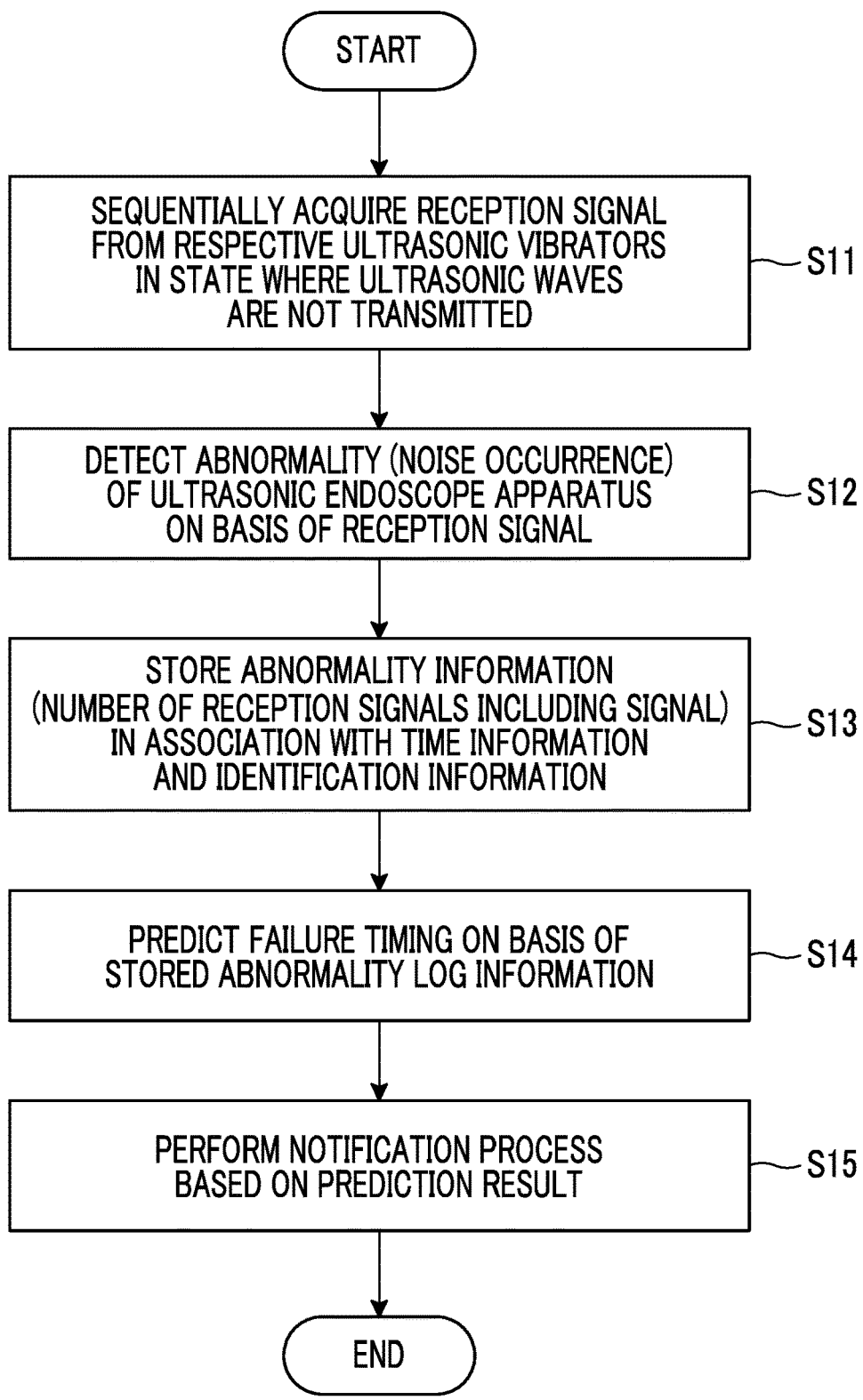
FIG. 12 is a flowchart for illustrating an operation of the failure prediction process of the system controller 152 shown in FIG. 8.

FIG. 12 is a flowchart for illustrating an operation of the failure prediction process of the system controller 152 shown in FIG. 8. First, the abnormality detection unit 152a controls the N ultrasonic vibrators 48 in a state where ultrasonic waves are not transmitted, and sequentially acquires reception signals from the respective N ultrasonic vibrators 48 (step S11).

Then, the abnormality detection unit 152a detects an abnormality that occurs in the ultrasonic endoscope apparatus 10 on the basis of each of the N reception signals acquired in step S11, and outputs the abnormality occurrence number as abnormality information (step S12).

Then, the storage control unit 152b stores the abnormality information output abnormality detection unit 152a in the ROM in association with time information at a current time point and identification information (hereinafter, referred to as identification information ID2) of the ultrasonic endoscope 12 connected to the main body (step S13).

Then, the failure prediction unit 152c predicts a failure timing of the ultrasonic endoscope apparatus 10 on the basis of the entire abnormality log information (abnormality information and time information) corresponding to the identification information ID2 stored in the ROM (step S14).

In a case where the failure timing is predicted in step S14, the notification control unit 152d performs the notification process based on the prediction result (step S15). The above-described series of processes are performed whenever time the ultrasonic endoscope 12 is connected to the main body, for example. Further, as the abnormality log information stored in the ROM increases, the prediction accuracy of the failure timing is also improved.

As described above, according to the ultrasonic endoscope apparatus 10 of the first modification example, it is possible to predict a failure timing of the ultrasonic endoscope apparatus 10 on the basis of a history of the abnormality occurrence number detected on the basis of the reception signals of the ultrasonic vibrators 48 of the ultrasonic endoscope 12. Thus, it is possible to predict the failure timing, to thereby propose an appropriate maintenance timing to the user. As a result, for example, it is possible to expect execution of maintenance before failure occurs, and to lengthen the life of the ultrasonic endoscope apparatus 10. Further, in a case where the abnormality occurrence number does not increase, it is possible to postpone the maintenance timing, and to reduce the number of maintenances to reduce a period of time during which the ultrasonic endoscope 12 or the main body cannot be used.

In the first modification example, a configuration in which the abnormality detection unit 152a acquires a reception signal of each of the N ultrasonic vibrators 48 in a state where ultrasonic waves are not transmitted has been described, but the invention is not limited thereto. A configuration in which the abnormality detection unit 152a acquires reception signals from at least two ultrasonic vibrators 48 among the N ultrasonic vibrators 48 in a state where ultrasonic waves are not transmitted and determines an abnormality on the basis of the acquired reception signals may be employed. In this case, similarly, it is possible to determine whether or not an abnormality occurrence number tends to increase on the basis of a history of abnormality information. Thus, it is possible to predict a failure timing.

Further, in the first modification example, a configuration in which the abnormality detection unit 152a outputs the number of reception signals (first number) including signals having a level that exceeds the threshold value TH3 among the N reception signals as abnormality information has been described. As a modification example thereof, a configuration in which the abnormality detection unit 152a calculates an abnormality occurrence rate that is a ratio of the first number to N or an abnormality non-occurrence rate that is a ratio of (N−(first number)) to N and outputs the result as abnormality information may be employed. In this case, in a case where the abnormality occurrence rate tends to increase, the failure prediction unit 152c is able to predict a failure timing based on the increase tendency. Further, in a case where the failure non-occurrence rate tends to decrease, the failure prediction unit 152c is able to predict a failure timing based on the decrease tendency.

Second Modification Example

Functional blocks of the system controller 152 in the ultrasonic endoscope apparatus 10 according to a second modification example are the same as in FIG. 8, but the functions of the abnormality detection unit 152a and the failure prediction unit 152c are partially different. In the second modification example, similarly, the system controller 152 configures a failure prediction system of the ultrasonic endoscope apparatus.

The abnormality detection unit 152a in the second modification example is the same as that in the first modification example in view of detection of an abnormality of the ultrasonic endoscope apparatus 10 on the basis of N reception signals in a state where ultrasonic waves are not transmitted, acquired as described in the first modification example, but its abnormality determination method is different from that in the first modification example.

Figure 13:
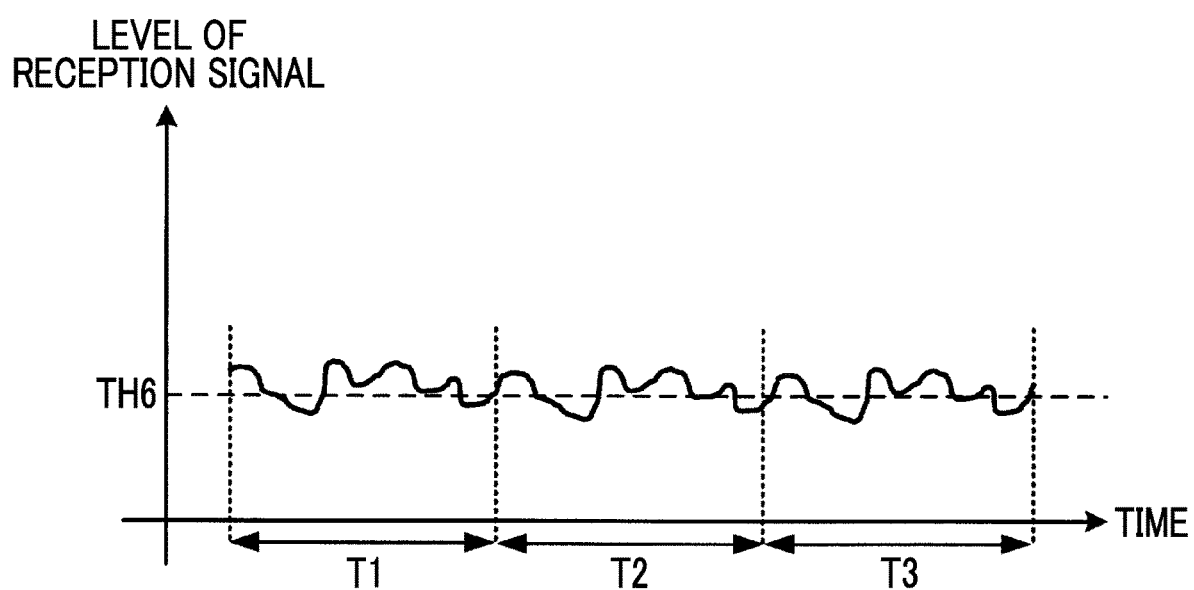
FIG. 13 is a diagram showing an example of a reception signal acquired in a case where ultrasonic waves are not transmitted.

FIG. 13 is a diagram showing an example of a reception signal acquired in a case where ultrasonic waves are not transmitted. Noise may be superimposed on the reception signal as a whole depending on a cause of an abnormality of the ultrasonic endoscope apparatus 10, and there is a case where an average level of the reception signals increases compared with the state of FIG. 9, as shown in FIG. 13. Further, in a case where the average level becomes too high (for example, reaches a predetermined threshold value TH5), there is a possibility that the quality of an ultrasound image may not be maintained. Thus, the abnormality detection unit 152a in the second modification example calculates an average level of N reception signals, determines that there is an abnormality in a case where the average level exceeds a predetermined threshold value TH6 (here, a value smaller than the threshold value TH5), and determines that there is no abnormality in a case where the average level is equal to or smaller than the threshold value TH6.

Further, in a case where it is determined that there is the abnormality, the abnormality detection unit 152a outputs the average level of the N reception signals as abnormality information. The threshold value TH6 configures a second threshold value. It is preferable that the threshold value TH6 is not common to all the ultrasonic endoscopes 12 connectable to the main body but is determined individually for each ultrasonic endoscope 12.

The failure prediction unit 152c in the second modification example predicts occurrence of a failure of the ultrasonic endoscope apparatus 10 on the basis of a plurality of pieces of abnormality log information corresponding to each piece of identification information stored in the ROM by the storage control unit 152b.

Figure 14:
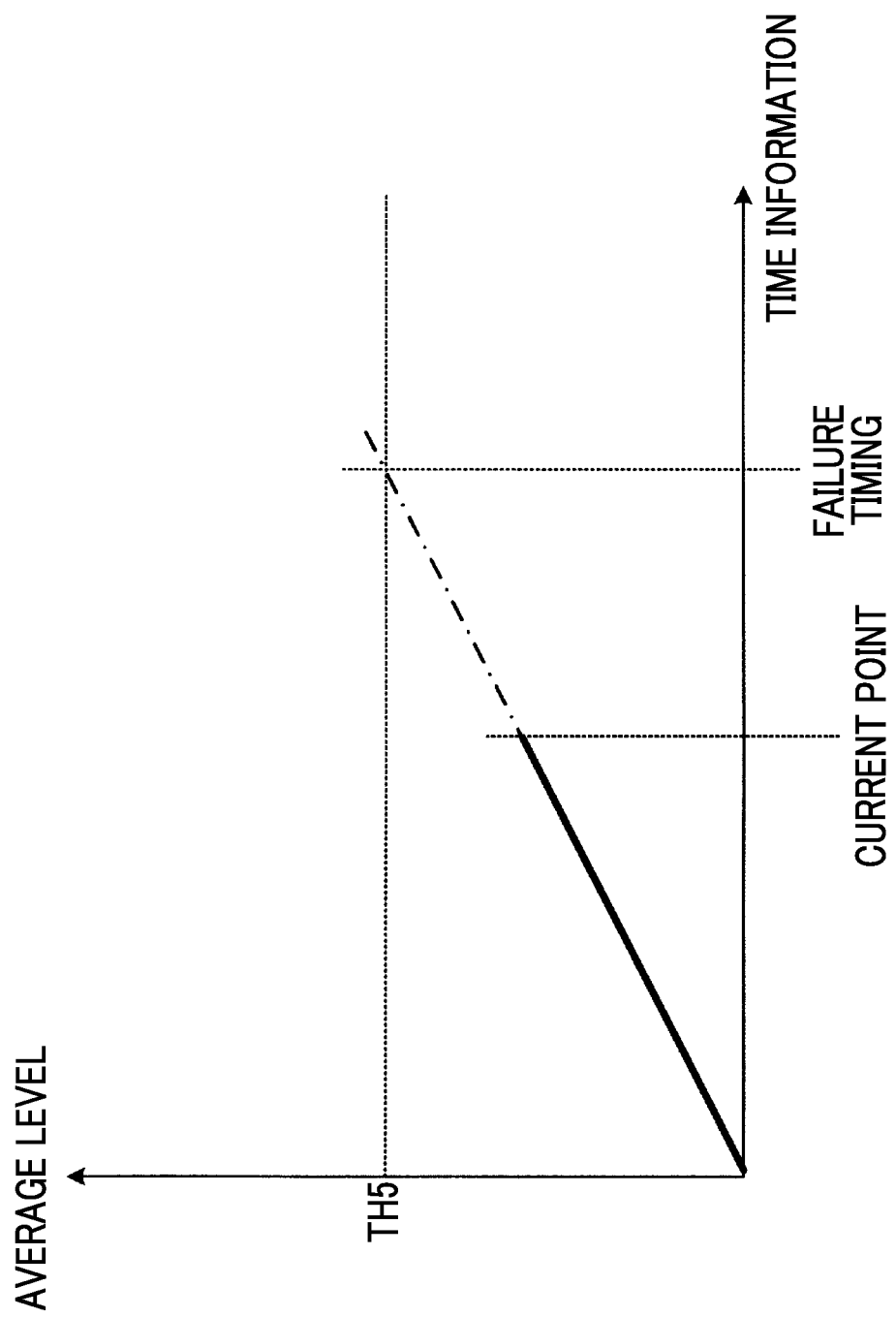
FIG. 14 is a graph showing an example of abnormality log information corresponding to unspecified identification information.

FIG. 14 is a graph showing an example of abnormality log information corresponding to unspecified identification information. In FIG. 14, a lateral axis represents time information included in abnormality log information, and a longitudinal axis represents abnormality information (average level of N reception signals) included in the abnormality log information. The threshold value TH5 shown in FIG. 14 is a lower limit value of the average level capable of determining that the ultrasonic endoscope apparatus 10 is in failure.

For example, in a case where there is almost no change in an average level based on the abnormality log information (for example, in a case where an inclination of an approximate straight line of the average level obtained from the abnormality log information by the least squares method is equal to or smaller than a predetermined value), the failure prediction unit 152c in the second modification example determines that a date obtained by adding a service life in normal use set in the ultrasonic endoscope 12 to a date based on the oldest time information included in the abnormality log information as a failure timing at which failure of the ultrasonic endoscope 12 occurs. Further, the failure prediction unit 152c determines a timing obtained by adding a time obtained by subtracting an accumulated usage time at a current time point of the ultrasonic endoscope apparatus 10 from an accumulated usable time in normal use that is determined in advance with respect to the ultrasonic endoscope apparatus 10 (a usable time until maintenance is necessary) to the current time point, as a failure timing at which failure of the main body of the ultrasonic endoscope apparatus 10 occurs.

Further, for example, in a case where there is a large increase tendency in the average level based on the abnormality log information (for example, in a case where the inclination of the approximate straight line exceeds the predetermined value), on the basis of the increase tendency, the failure prediction unit 152c determines a timing (failure timing in FIG. 14) at which the average level will reach the threshold value TH5 in the future (at which the ultrasonic endoscope apparatus 10 will fail) in a case where a usage frequency and a usage way up to a current time point are continued.

The failure prediction unit 152c outputs the failure timing of the ultrasonic endoscope apparatus 10 determined as described above as a prediction result.

Figure 15:
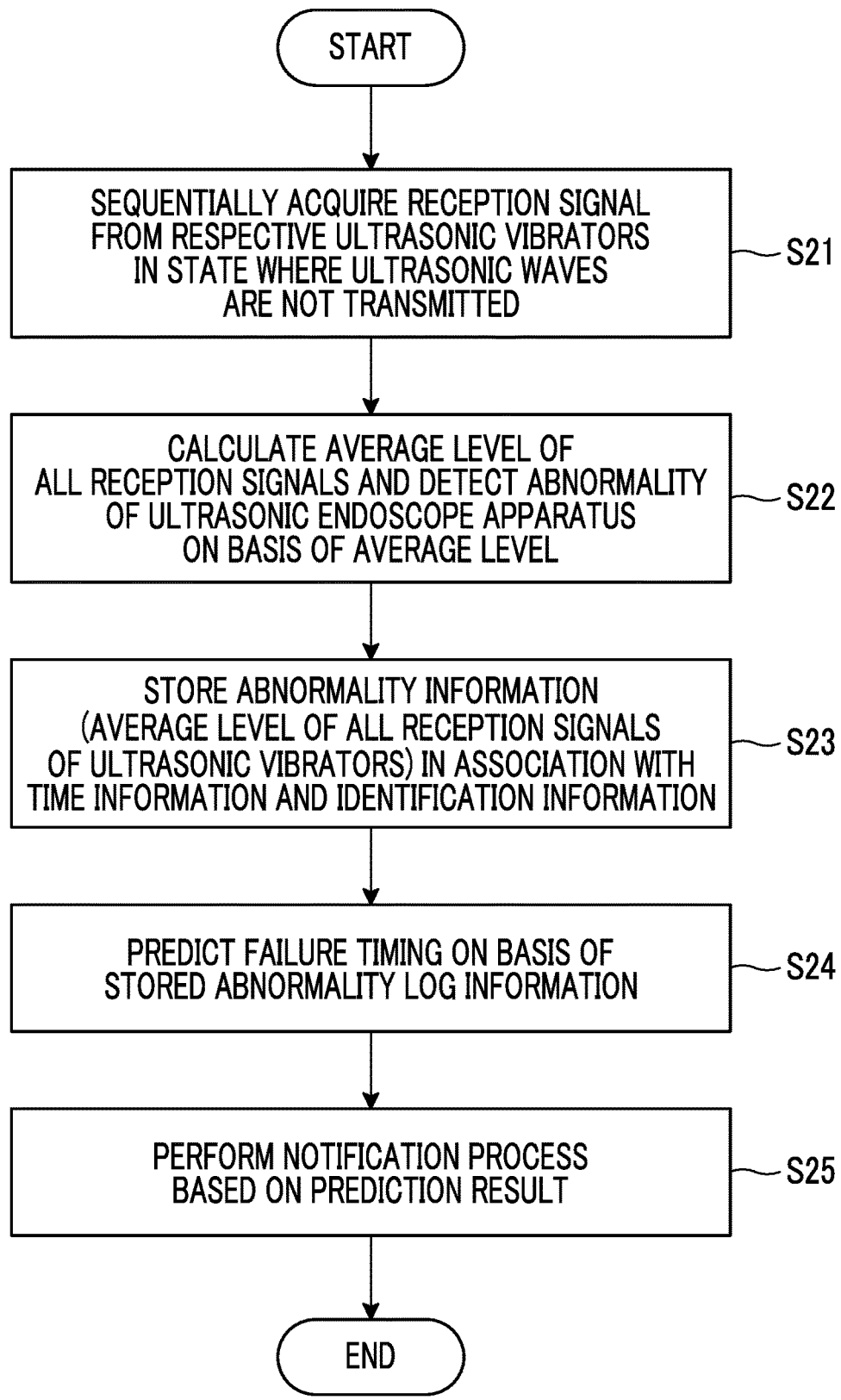
FIG. 15 is a flowchart for illustrating a failure prediction process of the system controller 152 in an ultrasonic endoscope apparatus 10 according to a second modification example.

FIG. 15 is a flowchart for illustrating a failure prediction process of the system controller 152 in the ultrasonic endoscope apparatus 10 according to the second modification example. First, the abnormality detection unit 152a controls the N ultrasonic vibrators 48 in a state where ultrasonic waves are not transmitted, and sequentially acquires reception signals from the respective N ultrasonic vibrators 48 (step S21).

Then, the abnormality detection unit 152a detects an abnormality that occurs in the ultrasonic endoscope apparatus 10 on the basis of an average level of the N reception signals acquired in step S21, and outputs the average level of the N reception signals as abnormality information in a case where it is determined that there is the abnormality (step S22).

Then, the storage control unit 152b stores the abnormality information output from the abnormality detection unit 152a in the ROM in association with time information at a current time point and identification information (hereinafter, referred to as identification information ID3) of the ultrasonic endoscope 12 connected to the main body (step S23).

Then, the failure prediction unit 152c predicts a failure timing of the ultrasonic endoscope apparatus 10 on the basis of the entire abnormality log information (abnormality information and time information) corresponding to the identification information ID3 stored in the ROM (step S24).

In a case where the failure timing is predicted in step S24, the notification control unit 152d performs a notification process based on the prediction result (step S25). The above-described series of processes are performed whenever time the ultrasonic endoscope 12 is connected to the main body, for example. Further, as the abnormality log information stored in the ROM increases, the prediction accuracy of the failure timing is also improved.

As described above, according to the ultrasonic endoscope apparatus 10 of the second modification example, it is possible to predict a failure timing of the ultrasonic endoscope apparatus 10 on the basis of a history of the average level of the reception signals of the ultrasonic vibrators 48 of the ultrasonic endoscope 12. Thus, it is possible to predict a failure timing, and to provide an appropriate maintenance timing to the user. As a result, for example, it is possible to expect execution of maintenance before failure occurs, and to lengthen the life of the ultrasonic endoscope apparatus 10. Further, in a case where the average level of the reception signals does not increase, it is possible to postpone the maintenance timing, and to reduce the times of maintenances to reduce a period of time during which the ultrasonic endoscope 12 or the main body cannot be used.

In the second modification example, a configuration in which the abnormality detection unit 152a acquires a reception signal from each of the N ultrasonic vibrators 48 in a state where ultrasonic waves are not transmitted has been described, but the invention is not limited thereto. The abnormality detection unit 152a acquires a reception signal from at least one ultrasonic vibrator 48 among the N ultrasonic vibrators 48 in a state where ultrasonic waves are not transmitted, and may determine an abnormality on the basis of the magnitude of the average level of the acquired reception signals. In this case, similarly, it is possible to determine whether or not noise superimposed on a reception signal tends to increase as a whole on the basis of a history of abnormality information. Accordingly, it is possible to predict a failure timing.

The respective functional blocks of the system controller 152 in the first modification example and the second modification example may be configured to be provided in a processor included in the endoscope processor device 16. Alternatively, among the functional blocks of the system controller 152, the failure prediction unit 152c and the notification control unit 152d may be configured to be provided in a processor included in an external device such as an external server that is connectable to the ultrasonic endoscope apparatus 10.

As described above, the following content is disclosed in this specification.

(1) A failure prediction system of an ultrasonic endoscope apparatus comprising:
- an abnormality detection unit that acquires a reception signal of an ultrasonic vibrator of an ultrasonic endoscope and detects an abnormality of the ultrasonic endoscope apparatus including the ultrasonic endoscope on the basis of the reception signal;
- a storage control unit that stores information on the abnormality detected by the abnormality detection unit in association with time information; and
- a failure prediction unit that predicts a failure timing of the ultrasonic endoscope apparatus on the basis of a plurality of pieces of the abnormality information stored by the storage control unit and the time information corresponding to the plurality of pieces of abnormality information.

(2) The failure prediction system of the ultrasonic endoscope apparatus according to (1),
wherein the abnormality detection unit acquires the reception signal of the ultrasonic vibrator in a state where ultrasonic waves are not transmitted from the ultrasonic vibrator, and detects the abnormality on the basis of the reception signal.

(3) The failure prediction system of the ultrasonic endoscope apparatus according to (2),
wherein the abnormality detection unit acquires the reception signal of each of a plurality of the ultrasonic vibrators included in the ultrasonic endoscope, determines that there is the abnormality in a case where the reception signal including a signal of a level that exceeds a predetermined first threshold value is present, and outputs a first number of the reception signals including the signal of the level that exceeds the first threshold value, a ratio of the first number to a second number of the plurality of ultrasonic vibrators, or a ratio of a number obtained by subtracting the first number from the second number to the second number, as the abnormality information.

(4) The failure prediction system of the ultrasonic endoscope apparatus according to (2),
wherein the abnormality detection unit determines that there is the abnormality in a case where an average level of the reception signals exceeds a predetermined second threshold value, and outputs the average level as the abnormality information.

(5) The failure prediction system of the ultrasonic endoscope apparatus according to (1),
wherein the abnormality detection unit acquires the reception signal of the ultrasonic vibrator that receives reflected waves of ultrasonic waves transmitted from all the ultrasonic vibrators included in the ultrasonic endoscope, and detects the abnormality of the ultrasonic endoscope on the basis of the reception signal.

(6) The failure prediction system of the ultrasonic endoscope apparatus according to any one of (1) to (5),
wherein the abnormality detection unit detects the abnormality in a period during which the ultrasonic endoscope is not used.

(7) The failure prediction system of the ultrasonic endoscope apparatus according to any one of (1) to (6),
wherein the storage control unit stores the abnormality information in association with identification information of the ultrasonic endoscope, and
wherein the failure prediction unit predicts the failure timing of the ultrasonic endoscope specified by the identification information on the basis of the abnormality information corresponding to the identification information and the time information.

(8) The failure prediction system of the ultrasonic endoscope apparatus according to any one of (1) to (7), further comprising:
a notification control unit that performs a notification process based on a prediction result of the failure prediction unit.

(9) The failure prediction system of the ultrasonic endoscope apparatus according to any one of (1) to (8),
wherein the abnormality detection unit, the storage control unit, and the failure prediction unit are provided in a main body of the ultrasonic endoscope apparatus.

(10) The failure prediction system of the ultrasonic endoscope apparatus according to any one of (1) to (8),
wherein the abnormality detection unit and the storage control unit are provided in a main body of the ultrasonic endoscope apparatus, and
wherein the failure prediction unit is provided in an external device connectable to the ultrasonic endoscope apparatus.

(11) A failure prediction method of an ultrasonic endoscope apparatus, comprising:
- an abnormality detection step of acquiring a reception signal of an ultrasonic vibrator of an ultrasonic endoscope and detecting an abnormality of the ultrasonic endoscope apparatus including the ultrasonic endoscope on the basis of the reception signal;
- a storage control step of storing information on the abnormality detected in the abnormality detection step in association with time information; and
- a failure prediction step of predicting a failure timing of the ultrasonic endoscope apparatus on the basis of a plurality of pieces of the abnormality information stored in the storage control step and the time information corresponding to the plurality of pieces of abnormality information.

(12) A non-transitory computer readable recording medium storing a failure prediction program of an ultrasonic endoscope apparatus, for causing a computer to execute:
- an abnormality detection step of acquiring a reception signal of an ultrasonic vibrator of an ultrasonic endoscope and detecting an abnormality of the ultrasonic endoscope apparatus including the ultrasonic endoscope on the basis of the reception signal;
- a storage control step of storing information on the abnormality detected in the abnormality detection step in association with time information; and a failure prediction step of predicting a failure timing of the ultrasonic endoscope apparatus on the basis of a plurality of pieces of the abnormality information stored in the storage control step and the time information corresponding to the plurality of pieces of abnormality information.

EXPLANATION OF REFERENCES

10: ultrasonic endoscope apparatus
12: ultrasonic endoscope
14: ultrasonic processor device
16: endoscope processor device
18: light source device
20: monitor
21a: water supply tank
21b: suction pump
21c: air supply pump
22: insertion part
24: operation part
26: universal cord
28a: air/water supply button
28b: suction button
30: treatment instrument insertion port
32a: ultrasound connector
32b: endoscope connector
32c: light source connector
36: ultrasound observation part
37: balloon
38: endoscope observation part
40: distal end part
42: bending part
43: flexible part
44: treatment instrument outlet
45: treatment instrument channel
46: ultrasonic vibrator unit
47: water supply port
48: ultrasonic vibrator
50: ultrasonic vibrator array
54: backing material layer
56: coaxial cable
60: FPC
76: acoustic matching layer
78: acoustic lens
82: observation window
84: objective lens
86: imaging element
88: illumination window
100: console
140: multiplexer
142: reception circuit
144: transmission circuit
146: A/D converter
148: image processing section
152: system controller
152A: abnormality detection unit
152a: abnormality detection unit
152B: storage control unit
152b: storage control unit
152C: failure prediction unit
152c: failure prediction unit
152D: notification control unit
152d: notification control unit
SG: noise signal

What is claimed is:

1. A non-transitory computer readable recording medium storing a failure prediction program of an ultrasonic endoscope apparatus including a monitor and an ultrasonic endoscope having a plurality of ultrasonic vibrators arranged in a convexly curved shape and a plurality of electrodes respectively connected to each of the plurality of ultrasonic vibrators, wherein the plurality of electrodes are connected to a flexible printed circuit and a plurality of coaxial cables, for causing a computer to execute:

a transmitting step of controlling the plurality of ultrasonic vibrators to sequentially transmit ultrasonic waves respectively from each of the plurality of ultrasonic vibrators;

an abnormality detection step of acquiring a plurality of reception signals of reflected waves of ultrasonic waves from the plurality of ultrasonic vibrators and detecting an abnormality of the ultrasonic endoscope apparatus based on the plurality of the reception signals;

a storage control step of storing information on the abnormality detected in the abnormality detection step in association with time information;

a failure prediction step of predicting a failure timing of the ultrasonic endoscope apparatus based on a plurality of pieces of the information on the abnormality stored in the storage control step and the time information corresponding to the plurality of pieces of the information on the abnormality, the failure timing being a date when an abnormality occurrence number will reach a predetermined threshold in future; and a notification step of maintaining the ultrasonic endoscope by displaying a message indicating a recommended maintenance timing of the ultrasonic endoscope based on the predicted failure timing on the monitor to notify a user of the recommended maintenance timing.

2. A failure prediction system of an ultrasonic endoscope apparatus, the failure prediction system comprising:

an ultrasonic endoscope apparatus having a monitor and a plurality of ultrasonic vibrators arranged in a convexly curved shape;

a plurality of electrodes respectively connected to each of the plurality of ultrasonic vibrators, wherein the plurality of electrodes are connected to a flexible printed circuit and a plurality of coaxial cables; and a processor configured to:
control the plurality of ultrasonic vibrators to sequentially transmit ultrasonic waves respectively from each of the plurality of ultrasonic vibrators;
acquire a plurality of reception signals of reflected waves of ultrasonic waves from the plurality of ultrasonic vibrators;
detect an abnormality of the ultrasonic endoscope apparatus based on the plurality of the reception signals;
store information on the abnormality detected, in association with time information;
predict a failure timing of the ultrasonic endoscope apparatus based on a plurality of pieces of the information on the abnormality and the time information corresponding to the plurality of pieces of the information on the abnormality, the failure timing being a date when an abnormality occurrence number will reach a predetermined threshold in future; and
display a message indicating a recommended maintenance timing of the ultrasonic endoscope based on the predicted failure timing on the monitor to notify a user of the recommended maintenance timing.

3. The failure prediction system of the ultrasonic endoscope apparatus according to claim 2, wherein the processor acquires the plurality of reception signals of each of the plurality of ultrasonic vibrators in a state where the ultrasonic waves are not transmitted from the plurality of ultrasonic vibrators, and detects the abnormality based on the plurality of reception signals.

4. The failure prediction system of the ultrasonic endoscope apparatus according to claim 3,
wherein the processor acquires the plurality of reception signals of each of the plurality of the ultrasonic vibrators included in the ultrasonic endoscope, determines that there is the abnormality in a case where the plurality of reception signals including a signal of a level that exceeds a predetermined first threshold value is present, and outputs a first number of the plurality of reception signals including the signal of the level that exceeds the predetermined first threshold value, a ratio of the first number to a second number of the plurality of ultrasonic vibrators, or a ratio of a number obtained by subtracting the first number from the second number to the second number, as the information on the abnormality.

5. The failure prediction system of the ultrasonic endoscope apparatus according to claim 4,
wherein the processor detects the abnormality in a period during which the ultrasonic endoscope is not used, the period during which the ultrasonic endoscope is not used being at least one of
a period until an inspection starting instruction to the ultrasonic endoscope is received,
a period during which a change in an endoscope image acquired from the ultrasonic endoscope is small,
a period during which an amount of motion of the ultrasonic endoscope that is obtained from a motion sensor provided in the ultrasonic endoscope is smaller than a predetermined value, and
a period during which the ultrasonic endoscope apparatus is set to a maintenance mode in a case where the maintenance mode is provided in the ultrasonic endoscope apparatus.

6. The failure prediction system of the ultrasonic endoscope apparatus according to claim 4,
wherein the processor stores the information on the abnormality in association with identification information of the ultrasonic endoscope, and predicts the failure timing of the ultrasonic endoscope specified by the identification information based on the information on the abnormality corresponding to the identification information and the time information.

7. The failure prediction system of the ultrasonic endoscope apparatus according to claim 3,
wherein the processor calculates an average level of the plurality of the reception signals acquired from the plurality of ultrasonic vibrators and determines that there is the abnormality in a case where the average level exceeds a predetermined second threshold value, and outputs the average level as the information on the abnormality.

8. The failure prediction system of the ultrasonic endoscope apparatus according to claim 7,
wherein the processor detects the abnormality in a period during which the ultrasonic endoscope is not used, the period during which the ultrasonic endoscope is not used being at least one of
a period until an inspection starting instruction to the ultrasonic endoscope is received,
a period during which a change in an endoscope image acquired from the ultrasonic endoscope is small,
a period during which an amount of motion of the ultrasonic endoscope that is obtained from a motion sensor provided in the ultrasonic endoscope is smaller than a predetermined value, and
a period during which the ultrasonic endoscope apparatus is set to a maintenance mode in a case where the maintenance mode is provided in the ultrasonic endoscope apparatus.

9. The failure prediction system of the ultrasonic endoscope apparatus according to claim 7,
wherein the processor stores the information on the abnormality in association with identification information of the ultrasonic endoscope, and predicts the failure timing of the ultrasonic endoscope specified by the identification information based on the information on the abnormality corresponding to the identification information and the time information.

10. The failure prediction system of the ultrasonic endoscope apparatus according to claim 3,
wherein the processor detects the abnormality in a period during which the ultrasonic endoscope is not used, the period during which the ultrasonic endoscope is not used being at least one of
a period until an inspection starting instruction to the ultrasonic endoscope is received,
a period during which a change in an endoscope image acquired from the ultrasonic endoscope is small,
a period during which an amount of motion of the ultrasonic endoscope that is obtained from a motion sensor provided in the ultrasonic endoscope is smaller than a predetermined value, and
a period during which the ultrasonic endoscope apparatus is set to a maintenance mode in a case where the maintenance mode is provided in the ultrasonic endoscope apparatus.

11. The failure prediction system of the ultrasonic endoscope apparatus according to claim 3,
wherein the processor stores the information on the abnormality in association with identification information of the ultrasonic endoscope, and predicts the failure timing of the ultrasonic endoscope specified by the identification information based on the information on the abnormality corresponding to the identification information and the time information.

12. The failure prediction system of the ultrasonic endoscope apparatus according to claim 2,
wherein the processor acquires the plurality of reception signals of each of the plurality of ultrasonic vibrators that receives the reflected waves of the ultrasonic waves transmitted from all of the plurality of ultrasonic vibrators included in the ultrasonic endoscope, and detects the abnormality of the ultrasonic endoscope apparatus based on the plurality of reception signals.

13. The failure prediction system of the ultrasonic endoscope apparatus according to claim 12,
wherein the processor detects the abnormality in a period during which the ultrasonic endoscope is not used, the period during which the ultrasonic endoscope is not used being at least one of
a period until an inspection starting instruction to the ultrasonic endoscope is received,
a period during which a change in an endoscope image acquired from the ultrasonic endoscope is small,
a period during which an amount of motion of the ultrasonic endoscope that is obtained from a motion sensor provided in the ultrasonic endoscope is smaller than a predetermined value, and a period during which the ultrasonic endoscope apparatus is set to a maintenance mode in a case where the maintenance mode is provided in the ultrasonic endoscope apparatus.

14. The failure prediction system of the ultrasonic endoscope apparatus according to claim 2, wherein the processor detects the abnormality in a period during which the ultrasonic endoscope is not used, the period during which the ultrasonic endoscope is not used being at least one of a period until an inspection starting instruction to the ultrasonic endoscope is received, a period during which a change in an endoscope image acquired from the ultrasonic endoscope is small, a period during which an amount of motion of the ultrasonic endoscope that is obtained from a motion sensor provided in the ultrasonic endoscope is smaller than a predetermined value, and a period during which the ultrasonic endoscope apparatus is set to a maintenance mode in a case where the maintenance mode is provided in the ultrasonic endoscope apparatus.

15. The failure prediction system of the ultrasonic endoscope apparatus according to claim 2, wherein the processor stores the information on the abnormality in association with identification information of the ultrasonic endoscope, and predicts the failure timing of the ultrasonic endoscope specified by the identification information based on the information on the abnormality corresponding to the identification information and the time information.

16. The failure prediction system of the ultrasonic endoscope apparatus according to claim 2, wherein the processor is provided in a main body of the ultrasonic endoscope apparatus.

17. The failure prediction system of the ultrasonic endoscope apparatus according to claim 2, wherein the processor includes a first processor and a second processor, the first processor being configured to:

drive the plurality of ultrasonic vibrators to transmit the ultrasonic waves, acquire the plurality of reception signals of the reflected waves of the ultrasonic waves from each of the plurality of ultrasonic vibrators, detect the abnormality of the ultrasonic endoscope apparatus including the ultrasonic endoscope based on the plurality of reception signals, store the information on the abnormality which was detected in association with the time information, and be provided in a main body of the ultrasonic endoscope apparatus, and the second processor being configured to:

predict the failure timing of the ultrasonic endoscope apparatus based on the plurality of pieces of the information on the abnormality and the time information corresponding to the plurality of pieces of the information on the abnormality, and be provided in an external device connectable to the ultrasonic endoscope apparatus.

18. A failure prediction method of the ultrasonic endoscope apparatus according to claim 2, the ultrasonic endoscope apparatus including the monitor and the ultrasonic endoscope having the plurality of ultrasonic vibrators arranged in the convexly curved shape and the plurality of electrodes respectively connected to each of the plurality of ultrasonic vibrators, wherein the plurality of electrodes are connected to the flexible printed circuit and the plurality of coaxial cables, comprising:

a transmitting step of controlling the plurality of ultrasonic vibrators to sequentially transmit the ultrasonic waves respectively from each of the plurality of ultrasonic vibrators;

an abnormality detection step of acquiring the plurality of reception signals of the reflected waves of the ultrasonic waves from the plurality of ultrasonic vibrators and detecting the abnormality of the ultrasonic endoscope apparatus based on the plurality of the reception signals;

a storage control step of storing the information on the abnormality detected in the abnormality detection step in association with the time information;

a failure prediction step of predicting the failure timing of the ultrasonic endo scope apparatus based on the plurality of pieces of the information on the abnormality stored in the storage control step and the time information corresponding to the plurality of pieces of the information on the abnormality, the failure timing being the date when the abnormality occurrence number will reach the predetermined threshold in the future; and a notification step of maintaining the ultrasonic endoscope by displaying a message indicating the recommended maintenance timing of the ultrasonic endoscope based on the predicted failure timing on the monitor to notify a user of the recommended maintenance timing.

* * * * *